United States Patent
Lee et al.

(10) Patent No.: US 12,077,572 B2
(45) Date of Patent: Sep. 3, 2024

(54) MONOCLONAL ANTIBODY FOR SPIKE PROTEIN OF MIDDLE EAST RESPIRATORY SYNDROME CORONAVIRUS, AND USE THEREOF

(71) Applicants: The United States of America, as represented by the Secretary, Department of Health and Human Services, Bethesda, MD (US); Korea (Center for Disease Control and Prevention), Chungcheongbuk-do (KR)

(72) Inventors: Hansaem Lee, Chungcheongbuk-do (KR); Janghoon Choi, Chungcheongbuk-do (KR); Sungsoon Kim, Chungcheongbuk-do (KR); Lingshu Wang, Bethesda, MD (US); Barney Graham, Bethesda, MD (US); John R Mascola, Bethesda, MD (US)

(73) Assignees: THE UNITED STATES OF AMERICA, AS REPRESENTED BY THE SECRETARY, DEPARTMENT OF HEALTH AND HUMAN SERVICES, Bethesda, MD (US); KOREA (CENTER FOR DISEASE CONTROL AND PREVENTION), Chungcheongbuk-do (KR)

( * ) Notice: Subject to any disclaimer, the term of this patent is extended or adjusted under 35 U.S.C. 154(b) by 123 days.

(21) Appl. No.: 17/952,308

(22) Filed: Sep. 25, 2022

(65) Prior Publication Data
US 2023/0265169 A1 Aug. 24, 2023

Related U.S. Application Data

(62) Division of application No. 16/641,580, filed as application No. PCT/KR2018/009754 on Aug. 23, 2018, now abandoned.

(30) Foreign Application Priority Data

Aug. 23, 2017 (KR) .......................... 10-2017-0106836

(51) Int. Cl.
*C07K 16/10* (2006.01)
*G01N 33/569* (2006.01)

(52) U.S. Cl.
CPC ....... *C07K 16/10* (2013.01); *G01N 33/56983* (2013.01); *C07K 2317/565* (2013.01); *C07K 2317/76* (2013.01); *G01N 2333/165* (2013.01)

(58) Field of Classification Search
None
See application file for complete search history.

(56) References Cited

U.S. PATENT DOCUMENTS

2021/0355193 A1  11/2021  Lee et al.

FOREIGN PATENT DOCUMENTS

| KR | 10-2016-0055164 A | 5/2016 | |
| KR | 10-2017-0005133 A | 1/2017 | |
| WO | 2015/057942 A1 | 4/2015 | |
| WO | WO-2015057942 A1 * | 4/2015 | ............. A61K 39/42 |

OTHER PUBLICATIONS

Lu et al., J Med Virol. Mar. 2017;89(3):542-545. doi: 10.1002/jmv.24652. Epub Aug. 22, 2016. PMID: 27486688 PMCID: PMC7166981.*
Janeway et al., Immunobology, 3rd edition, Garland Publishing Inc., 1997, pp. 3:26-3:31.*
Janeway et al., Immunobology, 3rd edition, Garland Publishing Inc., 1997, pp. 8:1-8:21.*
Darryl et al., I"nterferon-(Alfa)2b and ribavirin treatment improves outcome in MERS-COV-infected rhesus macaques," Nat Med. Author manuscript; October; 19(10): 1313-1317.
Edwards et al.,J Mol Biol. Nov. 14, 2003;334(1): 103-18.
Goel et al., J Immunol. Dec. 15, 2004; 173(12)7358-67.
International Search Report mailed Nov. 6, 2018 in PCT/KR2018/009754.
Jaffar, et al., "Ribavirin and interferon therapy in patients infected with the Middle East respiratory syndrome coronavirus: an observational study," International Journal of Infectious Diseases, 2014, pp. 42-46.
Janeway et al., Immunobiology, 3rd edition, Garland Publishing Inc., 1997, pp. 3:1-3:11.
Jiang, L et al. "Potent Neutralization of MERS-CoV by Human Neutralizing Monoclonal Antibodies to the Viral Spike Glycoprotein" Apr. 30, 2014, vol. 6 Issue 234 234ra59.
Kanyavuz et al., Nat Rev Immunol. Jun. 2019;19(6):355-368. doi: 10.1038/S41577-019-0126-7.
Lee, Hansaem et al., ;'Trend in Human Therapeutic MERS-CoV Antibody Development', Public Health Weekly Report, CDC, vol. 9 No. 37.

(Continued)

*Primary Examiner* — Michael Szperka
(74) *Attorney, Agent, or Firm* — Fredrikson & Byron, P.A.

(57) ABSTRACT

The present invention relates to monoclonal antibodies for a spike protein of the Middle East respiratory syndrome coronavirus (MERS-CoV), and a use thereof. Particularly, monoclonal antibodies 77-A5, 77-A6, 90-A3, 90-A9, 90-B2, 90-B7, 90-C4, 90-E5, 90-E6, 90-F1 and 90-F2 according to the present invention have excellent attachment force with respect to a full-length spike protein of MERS-CoV and the S1 domain of the protein, and, of the monoclonal antibodies, the monoclonal antibodies 90-F1, 90-E5, 90-E6, 90-F2, 77-A5 and 77-A6 have excellent attachment force with respect to an RBD antigen of MERS-CoV. Also, the antibodies 77-A5, 77-A6, 90-E5, 90-E6, 90-F1 and 90-F2 exhibit neutralizing capacity with respect to a MERS pseudovirus and MERS-CoV, and the antibodies 90-B2 and 90-B7 exhibit neutralizing capacity only with respect to MERS-CoV. Further, the monoclonal antibodies have a particular monomeric form, and have excellent stability and thus may be useful for treating or diagnosing MERS.

9 Claims, 14 Drawing Sheets

Specification includes a Sequence Listing.

(56) References Cited

OTHER PUBLICATIONS

Lescar, et al. Journal of Biological Chemistry 270.30 (1995): 18067-18076.
Llyod et al., Protein Eng Des Sei. Mar. 2009;22(3):159-68. doi: 10.1093/protein/gzn058. Epub Oct. 29, 2008.
Non-Final Office Action received for U.S. Appl. No. 16/641,580, mailed on May 24, 2022, 14 pages.
Office Action received for U.S. Appl. No. 16/641,580, mailed on Feb. 15, 2022, 7 pages.
Rudikoff et al., Proc Natl Acad Sci USA. Mar. 1982;79(6):1979-83.
Ying, T. et al., "Exceptionally Potent Neutralization of Middle East Respiratory Syndrome Coronavirus by Human Monoclonal Antibodies", Journal of Virology, Jul. 2014, vol. 88, No. 14. pp. 7796-7805.

\* cited by examiner

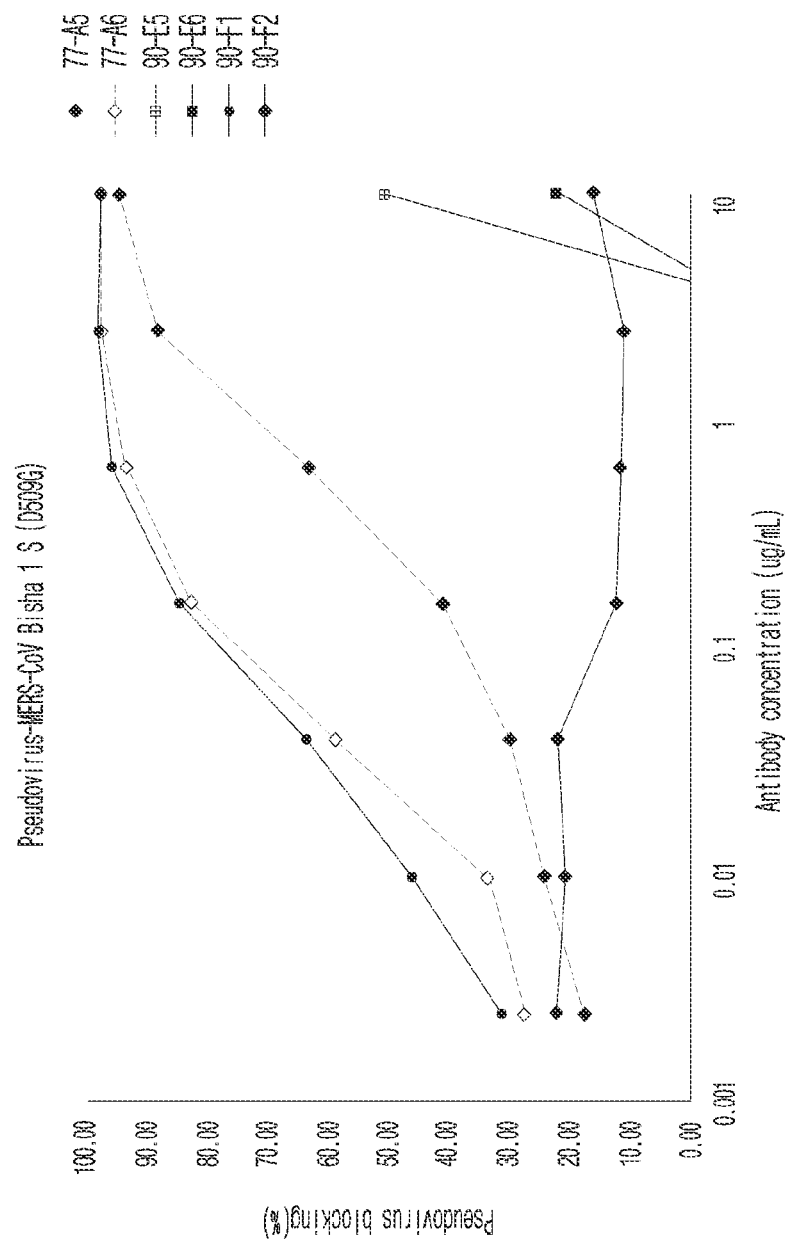

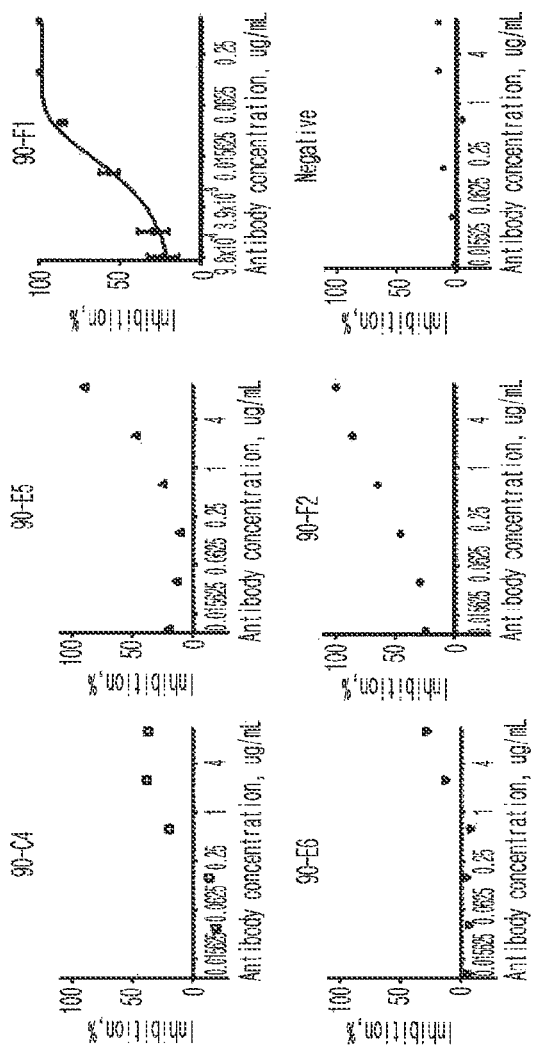

SEQUENCE LISTING

```
Sequence total quantity: 23
SEQ ID NO: 1                    moltype = AA  length = 136
FEATURE                         Location/Qualifiers
source                          1..136
                                mol_type = protein
                                organism = Homo sapiens
SEQUENCE: 1
TGVHSQVQLV QSGAEVKKPG SSVKVSCKAS GGTFRSHAIS WVRQAPGQGL EWMGGIIPIF    60
ASANYAQKFQ GRVTITADES TSTAYMDLSS LRSDDTAVYY CAKNVSPKSY SGRYSISYFY   120
GVDVWGQGTT VTVSSA                                                   136

SEQ ID NO: 2                    moltype = AA  length = 131
FEATURE                         Location/Qualifiers
source                          1..131
                                mol_type = protein
                                organism = Homo sapiens
SEQUENCE: 2
TGSWAQSALT QPPSASGTPG QRVTISCSGS SSNIGSNTVN WYQQLPGTAP KLLIYSNNQR    60
PSGVPDRFSG SKSGTSASLA ISGLQSEDEA DYYCAAWDDS LSGHYVFGTG TKVTVLGQPK   120
ANPTVTLFPP S                                                        131

SEQ ID NO: 3                    moltype = AA  length = 126
FEATURE                         Location/Qualifiers
source                          1..126
                                mol_type = protein
                                organism = Homo sapiens
SEQUENCE: 3
TGVHSEVQLL ESGGGLVQPG GSLRLSCADS GLTFSSYAMS WVRQAPGKGL EWVSAISVSG    60
GSTYYSDSVK GRFTISRDNS KNTLSLQMNS LRAEDTAVYY CVKARSIVGP FDYWGQGTLV   120
TVSSAS                                                              126

SEQ ID NO: 4                    moltype = AA  length = 130
FEATURE                         Location/Qualifiers
source                          1..130
                                mol_type = protein
                                organism = Homo sapiens
SEQUENCE: 4
TGSWAQSALT QPPSVSAAPG QKVTISCSGS SSNIGNNYVS WYQHLPGTAP KLLIYDNIMR    60
PSGIPDRFSG SKSGTSATLG ITGLQTGDEA DYYCGTWDTS LSAVVFGGGT KLTVLGQPKA   120
APSVTLFPPS                                                          130

SEQ ID NO: 5                    moltype = AA  length = 135
FEATURE                         Location/Qualifiers
source                          1..135
                                mol_type = protein
                                organism = Homo sapiens
SEQUENCE: 5
TGVHSQVQLV QSGAEVKKPG ASVKVSCMTS GYTFTSYGIS WVRQAPGQGL EWMGWISAYN    60
GNTNYAQKLQ GRVTMTTDTS TSTAYMELRS LRSDDTAVYY CARDRGAYWD CGGDCYLSAF   120
DYWGQGTLVT VSSAS                                                    135

SEQ ID NO: 6                    moltype = AA  length = 130
FEATURE                         Location/Qualifiers
source                          1..130
                                mol_type = protein
                                organism = Homo sapiens
SEQUENCE: 6
TGSNSQAVVT QPPSVSAAPG QKVTISCSGS SSNIGNNYVS WYQQLPGTAP KLLIYDNNKR    60
PSGIPDRFSG SKSGTSATLG ITGLQTGDEA DYYCGTWDSS LSAVVFGGGT KLTVLGQPKA   120
APSVTLFPPS                                                          130

SEQ ID NO: 7                    moltype = AA  length = 132
FEATURE                         Location/Qualifiers
source                          1..132
                                mol_type = protein
                                organism = Homo sapiens
SEQUENCE: 7
TGVHSQVQLV QSGAEVKKPG SSVKVSCKAS GGTFSSFPIS WVRQAPGQGL EWMGGIIPIF    60
GAANYAQKFQ GRVTITADES TSTAYMELSS LRSEDTAVYY CARNYEEIVV IPAIMNFGYW   120
GQGTLVTVSS AS                                                       132

SEQ ID NO: 8                    moltype = AA  length = 113
FEATURE                         Location/Qualifiers
source                          1..113
                                mol_type = protein
                                organism = Homo sapiens
SEQUENCE: 8
TGVHSEIVLT QSPGTLSLSP GERATLSCRA SQSVASSYLA WYQQKPGQAP RLLIYGTSSR    60
```

```
ATGIPDRFSG SGSGADFTLT ISRLEPEDFA VYYCQQYGTS PLTFGGGTKV EIK           113

SEQ ID NO: 9            moltype = AA   length = 130
FEATURE                 Location/Qualifiers
source                  1..130
                        mol_type = protein
                        organism = Homo sapiens
SEQUENCE: 9
TGVHSQVQLQ ESGPGLVKPS ETLSLTCTVS GGSISSSSYY WGWIRQPPGK GLEWIGSIYY    60
SGNTYYNPSL KSRVTISVDT SKNHFSLRLS SVTAADTAVY FCARSLPHYD STGYLLYWGQ   120
GTLVTVSSAS                                                          130

SEQ ID NO: 10           moltype = AA   length = 115
FEATURE                 Location/Qualifiers
source                  1..115
                        mol_type = protein
                        organism = Homo sapiens
SEQUENCE: 10
TGVHSEIVLT QSPATLSLSP GGRATLSCRA SQSVSRYLAW YQQKPGRAPR LLIYDASNRA    60
PGIPARFSGS GSGTDFTLTI SSLEPEDFAV YYCQQRSNWP QTTFGPGTKV DIKRT        115

SEQ ID NO: 11           moltype = AA   length = 135
FEATURE                 Location/Qualifiers
source                  1..135
                        mol_type = protein
                        organism = Homo sapiens
SEQUENCE: 11
TGVHSEVQLL ESGGGLVKPG GSLRLSCAAS GFTFGSYSMT WVRQAPGKGL EWVSSISSSS    60
SYIYYADSVK GRFTISRDNA KNSLFLQMNS LRAEDTAVYY CARGNGYCSH NSCYKIGVWF   120
DPWGQGTLVT VSSAS                                                    135

SEQ ID NO: 12           moltype = AA   length = 130
FEATURE                 Location/Qualifiers
source                  1..130
                        mol_type = protein
                        organism = Homo sapiens
SEQUENCE: 12
TGSNSQAVVT QPPSVSAAPG QKVTISCSGS SSNIGNNYVS WYQQLPGTAP KLLIYDNNKR    60
PSGIPDRFSG SKSGTSATLG ITGLQTGDEA DYYCGTWDSS LSAFVFGTGT KVTVLGQPKA   120
NPTVTLFPPS                                                          130

SEQ ID NO: 13           moltype = AA   length = 129
FEATURE                 Location/Qualifiers
source                  1..129
                        mol_type = protein
                        organism = Homo sapiens
SEQUENCE: 13
TGVHSQVQLQ ESGPGLVKPS GTLSLTCAVS GGSINSNWW SWVRQPPGKG LEWIGEIYYS     60
GSTNYNPSLK SRVTTSVDNS KNQFSLKLSS VTAADTAVYY CATFDSGGYN PNWFDPWGQG   120
TLVTVSSAS                                                           129

SEQ ID NO: 14           moltype = AA   length = 131
FEATURE                 Location/Qualifiers
source                  1..131
                        mol_type = protein
                        organism = Homo sapiens
SEQUENCE: 14
TGSWAQSALT QPPSVSGAPG QRVTISCTGS SSSIGAGYDV HWYQQLPGTA PKLLIYGNSN    60
RPSGVPDRFS GSKSGTSASL AITGLQAEDE ADYYCQSYDS SLSGYVFGTG TKVTVLGQPK   120
ANPTVTLFPP S                                                        131

SEQ ID NO: 15           moltype = AA   length = 132
FEATURE                 Location/Qualifiers
source                  1..132
                        mol_type = protein
                        organism = Homo sapiens
SEQUENCE: 15
TGVHSQVQLV QSGAEVKKPG SSVKVSCKAS GGTFSSYTIN WVRQAPGQGL EWMGGIIPIF    60
GTANYAQKFQ GRVTITADAS TSTAYMELSS LRSEDTAVYY CARVLLRSSS WFSSNWFDPW   120
GQGTLVTVSS AS                                                       132

SEQ ID NO: 16           moltype = AA   length = 130
FEATURE                 Location/Qualifiers
source                  1..130
                        mol_type = protein
                        organism = Homo sapiens
SEQUENCE: 16
TGSWAQSVLT QPPSVSGAPG QRVTISCTGS SSNIGAGYDV HWYQQLPGTA PKVLIYGNSN    60
RPSGVPDRFS GSKSDTSASL AITGLQAEDE ADYYCQSYDS SLSVVFGGGT KLTVLGQPKA   120
```

```
APSVTLFPPS                                                                  130

SEQ ID NO: 17           moltype = AA  length = 129
FEATURE                 Location/Qualifiers
source                  1..129
                        mol_type = protein
                        organism = Homo sapiens
SEQUENCE: 17
TGVHSEVQLV ESGGGLVQPG RSLRLSCAAS GFTFDDHAMH WVRQAPGKGL EWVSGFSWNS   60
GSIGYADSVK GRFTISRDNA KNSLYLQMNS LRAEDTALYY CAKDRRSDYY FYGMDVWGQG  120
TTVTVSSAS                                                          129

SEQ ID NO: 18           moltype = AA  length = 130
FEATURE                 Location/Qualifiers
source                  1..130
                        mol_type = protein
                        organism = Homo sapiens
SEQUENCE: 18
TGSWAQSVLT QPPSVSAAPG QKVTISCSGS RSNIGNNYVS WYQQLPGTAP KLLIYDNNKR   60
PSGIPDRFSG SKSGTSATLG ITGLQTGDEA DYYCGTWDSS LNAGVFGGGT KLTVLGQPKA  120
APSVTLFPPS                                                         130

SEQ ID NO: 19           moltype = AA  length = 138
FEATURE                 Location/Qualifiers
source                  1..138
                        mol_type = protein
                        organism = Homo sapiens
SEQUENCE: 19
TGVHSQVQLV QSGAEVKRPG SSVKVSCKTS GGTFNNNAIN WVRQAPGQGL EWMGGIIPFF   60
GIAKYAQKFQ GRVTITADES TSTAYMELSS LRSEDTAVYY CARDLPRESS YGSGSYYTHY  120
YAMDVWGQGT TVTVSSAS                                                138

SEQ ID NO: 20           moltype = AA  length = 115
FEATURE                 Location/Qualifiers
source                  1..115
                        mol_type = protein
                        organism = Homo sapiens
SEQUENCE: 20
TGVHSEIVLT QSPATLSLSP GERATLSCGA SQSVSSSYLA WYQQKPGLAP RLLIYDASSR   60
ATGIPDRFSG SGSGTDFTLT ISRLEPEDFA VYYCQQYGSS PLTFGGGTKV EIKRT        115

SEQ ID NO: 21           moltype = AA  length = 125
FEATURE                 Location/Qualifiers
source                  1..125
                        mol_type = protein
                        organism = Homo sapiens
SEQUENCE: 21
TGVHSQVQLV QSGAEVKKPG ASVKVSCKAS GYTFTTYYMH WVRQAPGQGL EWMGIINPSG   60
GSTSYAQKFQ GRVTMTRDTS TSTVYMELSS LRSEDTAVYY CARGAVVVIL DYWGQGTLVT  120
VSSAS                                                              125

SEQ ID NO: 22           moltype = AA  length = 114
FEATURE                 Location/Qualifiers
source                  1..114
                        mol_type = protein
                        organism = Homo sapiens
SEQUENCE: 22
TGVHSDIQMT QSPSTLSASV GDRVTITCRA SQTISTWLAW YQQKPGKAPK LLIYKASSLE   60
SGVPSRFSGS GSGTEFTLTI SSLQPDDFAT YYCQQYNSYS YTFGQGTKLE IKRT         114

SEQ ID NO: 23           moltype = AA  length = 1354
FEATURE                 Location/Qualifiers
REGION                  1..1354
                        note = middle east respiratory syndrome coronavirus spike
                         protein
VARIANT                 1354
source                  1..1354
                        mol_type = protein
                        organism = unidentified
SEQUENCE: 23
MIHSVFLLMF LLTPTESYVD VGPDSVKSAC IEVDIQQTFF DKTWPRPIDV SKADGIIYPQ   60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRLLSDD RTEVPQLVNA NQYSPCVSIV PSTVWEDGDY  540
```

-continued

```
YRKQLSPLEG GGWLVASGST VAMTEQLQMG FGITVQYGTD TNSVCPKLEF ANDTKIASQL    600
GNCVEYSLYG VSGRGVFQNC TAVGVRQQRF VYDAYQNLVG YYSDDGNYYC LRACVSVPVS    660
VIYDKETKTH ATLFGSVACE HISSTMSQYS RSTRSMLKRR DSTYGPLQTP VGCVLGLVNS    720
SLFVEDCKLP LGQSLCALPD TPSTLTPRSV RSVPGEMRLA SIAFNHPIQV DQLNSSYFKL    780
SIPTNFSFGV TQEYIQTTIQ KVTVDCKQYV CNGFQKCEQL LREYGQFCSK INQALHGANL    840
RQDDSVRNLF ASVKSSQSSP IIPGFGGDFN LTLLEPVSIS TGSRSARSAI EDLLFDKVTI    900
ADPGYMQGYD DCMQQGPASA RDLICAQYVA GYKVLPPLMD VNMEAAYTSS LLGSIAGVGW    960
TAGLSSFAAI PFAQSIFYRL NGVGITQQVL SENQKLIANK FNQALGAMQT GFTTTNEAFQ   1020
KVQDAVNNNA QALSKLASEL SNTFGAISAS IGDIIQRLDV LEQDAQIDRL INGRLTTLNA   1080
FVAQQLVRSE SAALSAQLAK DKVNECVKAQ SKRSGFCGQG THIVSFVVNA PNGLYFMHVG   1140
YYPSNHIEVV SAYGLCDAAN PTNCIAPVNG YFIKTNNTRI VDEWSYTGSS FYAPEPITSL   1200
NTKYVAPQVT YQNISTNLPP PLLGNSTGID FQDELDEFFK NVSTSIPNFG SLTQINTTLL   1260
DLTYEMLSLQ QVVKALNESY IDLKELGNYT YYNKWPWYIW LGFIAGLVAL ALCVFFILCC   1320
TGCGTNCMGK LKCNRCCDRY EEYDLEPHKV HVHX                              1354
```

MONOCLONAL ANTIBODY FOR SPIKE PROTEIN OF MIDDLE EAST RESPIRATORY SYNDROME CORONAVIRUS, AND USE THEREOF

CROSS-REFERENCE TO RELATED APPLICATIONS BACKGROUND OF THE INVENTION

This application is a divisional of U.S. Ser. No. 16/641,580, filed on Feb. 24, 2020, entitled "MONOCLONAL ANTIBODY FOR SPIKE PROTEIN OF MIDDLE EAST RESPIRATORY SYNDROME CORONAVIRUS, AND USE THEREOF," which is a nationalization of PCT Application No. PCT/KR2018/009754, filed on Aug. 23, 2018, entitled "MONOCLONAL ANTIBODY FOR SPIKE PROTEIN OF MIDDLE EAST RESPIRATORY SYNDROME CORONAVIRUS, AND USE THEREOF," which claims the benefit of and priority to Korean Patent Application No. 10-2017-0106836, filed on Aug. 23, 2017, the entirety of each of which is incorporated herein by reference.

INCORPORATION BY REFERENCE TO A SEQUENCE LISTING

This application includes a Sequence Listing XML submitted electronically in XML format. The Sequence Listing XML, created May 12, 2023, is named "18931.22.1 Sequence Listing.xml," which is 24.5 kb in size. The Sequence Listing XML replaces the content of the ASCII text file of the sequence listing named "18931-22_2020-02-24_Sequence-Listing_ST25," which is 40.0 kb in size, was created on Feb. 24, 2020 and electronically submitted via EFS-Web. The Sequence Listing XML herewith is incorporated herein by reference in its entirety.

1. FIELD OF THE INVENTION

The present invention relates to monoclonal antibodies for a spike protein of Middle East respiratory syndrome coronavirus and a use thereof.

2. DESCRIPTION OF THE RELATED ART

Middle East respiratory syndrome (MERS) was first identified in the Middle East region in September 2012. According to the report made by WHO, MERS spread to 26 countries as of Jun. 5, 2017, resulting in 1,980 confirmed patients and 693 deaths worldwide. It is a high-risk disease with a mortality rate of 35%.

Middle East respiratory syndrome coronavirus (MERS-CoV), the pathogen of MERS, is a newly discovered beta-coronavirus ($\gamma$CoV), which was first found in 2012. This virus is a 30-kb (+)-sense single-stranded RNA virus, and is similar to severe acute respiratory syndrome (SARS) virus. MERS-CoV penetrates into cells as being conjugated with a human DPP4 (dipeptidyl peptidase 4) receptor by using a spike protein (S protein) (Wang N, Shi X, Jiang L J, Zhang S, Wang D, Tong P, Guo D, et al., Cell Research. 2013:23: 986). MERS-CoV has a latency of about one week and causes severe respiratory symptoms such as high fever, coughing, and difficulty in breathing, etc.

For the treatment of MERS, the immunomodulator interferon and the anti-viral agent ribarvirin or lopinavir are used (Public Health England, ISARIC, 2015. Sep. 5. ver 3.0; Chung Y P, Song J Y, Seo Y B, et al., Infection & Chemotherapy. 2015). Interferon is an immune protein released when a virus or germ enters in a human body, inducing the surrounding cells to emit antiviral cytokines, inhibiting virus proliferation, and inviting immune cells to remove the virus-infected cells. However, the use of interferon can cause side effects such as bone marrow suppression, anemia, decrease of white cell number, or decrease of platelet number.

Ribarvirin, the antiviral agent, inhibits the proliferation of various types of viruses by interrupting the RNA synthesis thereof in the form of a nucleoside analogue. However, ribarvirin also induces side effects such as toxicity, carcinogenesis, or hemolytic anemia. The administration of interferon and ribarvirin for the treatment of MERS has not been supported by the clinical tests. In the rhesus monkey animal model, the co-administration of interferon and ribarvirin was effective in treating MERS (Falzarano D, Wit E, Rasmussen A L., et al., Nature Medicine, 2013, 19, 10, p 1313-1318). However, when interferon and ribarvirin were co-administered to 5 MERS patients with severe conditions in Middle East, the treatment effect was hardly observed (Al-Tawfiq J A, Momattin H., Dib J., et al., International Journal of Infectious Diseases 2014, 20, p 42-46). Therefore, it is urgently requested to develop a biologically safe therapeutic antibody that can be used for severe MERS patients, immunocompromised patients, and underlying disease patients with suppressing virus proliferation effectively.

In relation to the above, Korean Patent No 10-1593641 describes a monoclonal antibody binding specifically to MERS-CoV nucleocapsid and a composition for diagnosing MERS-CoV comprising the same.

Thus, the present inventors tried to develop therapeutic antibodies for MERS-CoV. As a result, the inventors succeeded in preparation of 24 kinds of monoclonal antibodies specifically binding to the spike protein of MERS-CoV. The inventors further confirmed that 11 antibodies (77-A5, 77-A6, 90-A3, 90-A9, 90-B2, 90-B7, 90-C4, 90-E5, 90-E6, 90-F1, and 90-F2) among them had excellent adhesion to MERS-CoV full-length spike and S1 antigen, and 90-F1, 90-E5, 90-E6, 90-F2, 77-A5, and 77-A6 antibodies demonstrated excellent adhesion to MERS-CoV RBD antigen. Also, 77-A5, 77-A6, 90-E5, 90-E6, 90-F1, and 90-F2 antibodies showed neutralizing ability against MERS pseudovirus and MERS-CoV, 90-B2 and 90-B7 antibodies showed neutralizing ability only against MERS-CoV. In addition, the present inventors further confirmed that the antibodies of the present invention are in the form of a certain monomer and have excellent physical stability, leading to the completion of the present invention.

SUMMARY OF THE INVENTION

It is an object of the present invention to provide a monoclonal antibody binding specifically to the spike protein of Middle East respiratory syndrome coronavirus.

It is another object of the present invention to provide a gene encoding the monoclonal antibody of the invention, a recombinant vector comprising thereof, and a host cell introduced with the gene or the recombinant vector above.

It is also an object of the present invention to provide a use of the prevention, treatment or diagnosis of Middle East respiratory syndrome comprising the monoclonal antibody of the invention.

It is further an object of the present invention to provide a kit for the detection or quantification of an antigen of Middle East respiratory syndrome comprising the monoclonal antibody of the invention.

To achieve the above objects, the present invention provides a heavy chain variable region of the monoclonal antibody specifically binding to the MERS-CoV spike protein whose complementarity determining region (CDR) is composed of the amino acid sequence represented by SEQ. ID. NO: 1, 3, 5, 7, 9, 11, 13, 15, 17, 19, or NO: 21.

The present invention also provides a gene encoding the heavy chain variable region of the monoclonal antibody of the invention.

The present invention also provides a recombinant vector comprising the gene encoding the heavy chain variable region of the monoclonal antibody of the invention.

The present invention also provides a host cell introduced with the gene encoding the heavy chain variable region of the monoclonal antibody of the invention or the recombinant vector comprising the gene above.

The present invention also provides a composition for the prevention, treatment or diagnosis of Middle East respiratory syndrome comprising the heavy chain variable region of the monoclonal antibody of the invention.

The present invention also provides a kit for the detection or quantification of an antigen of Middle East respiratory syndrome comprising the heavy chain variable region of the monoclonal antibody of the invention.

The present invention also provides a light chain variable region of the monoclonal antibody specifically binding to the MERS-CoV spike protein whose complementarity determining region (CDR) is composed of the amino acid sequence represented by SEQ. ID. NO: 2, 4, 6, 8, 10, 12, 14, 16, 18, 20, or NO: 22.

The present invention also provides a gene encoding the light chain variable region of the monoclonal antibody of the invention.

The present invention also provides a recombinant vector comprising the gene encoding the light chain variable region of the monoclonal antibody of the invention.

The present invention also provides a host cell introduced with the gene encoding the light chain variable region of the monoclonal antibody of the invention or the recombinant vector comprising the gene above.

The present invention also provides a composition for the prevention, treatment or diagnosis of Middle East respiratory syndrome comprising the light chain variable region of the monoclonal antibody of the invention.

The present invention also provides a kit for the detection or quantification of an antigen of Middle East respiratory syndrome comprising the light chain variable region of the monoclonal antibody of the invention.

The present invention also provides a monoclonal antibody specifically binding to the MERS-CoV spike protein containing a heavy chain variable region whose complementarity determining region is composed of the amino acid sequence represented by SEQ. ID. NO: 1, 3, 5, 7, 9, 11, 13, 15, 17, 19, or NO: 21, and a light chain variable region whose complementarity determining region is composed of the amino acid sequence represented by SEQ. ID. NO: 2, 4, 6, 8, 10, 12, 14, 16, 18, 20, or NO: 22.

The present invention also provides a gene encoding the monoclonal antibody of the invention.

The present invention also provides a recombinant vector containing the gene encoding the monoclonal antibody of the invention.

The present invention also provides a host cell introduced with the gene encoding the monoclonal antibody of the invention or the recombinant vector comprising the gene above.

The present invention also provides a composition for the prevention, treatment or diagnosis of Middle East respiratory syndrome comprising the monoclonal antibody of the invention.

The present invention provides a kit for the detection or quantification of an antigen of Middle East respiratory syndrome comprising the monoclonal antibody of the invention.

The present invention also provides a method for preventing, treating or diagnosing Middle East respiratory syndrome comprising a step of administering the heavy chain variable region of the monoclonal antibody of the invention to a subject.

The present invention also provides a use of the heavy chain variable region of the monoclonal antibody of the invention for the manufacture of a medicament for preventing, treating or diagnosing Middle East respiratory syndrome.

The present invention also provides a method for preventing, treating or diagnosing Middle East respiratory syndrome comprising a step of administering the light chain variable region of the monoclonal antibody of the invention to a subject.

The present invention also provides a use of the light chain variable region of the monoclonal antibody of the invention for the manufacture of a medicament for preventing, treating or diagnosing Middle East respiratory syndrome.

The present invention also provides a method for preventing, treating or diagnosing Middle East respiratory syndrome comprising a step of administering the monoclonal antibody of the invention to a subject.

In addition, the present invention provides a use of the monoclonal antibody of the invention for the manufacture of a medicament for preventing, treating or diagnosing Middle East respiratory syndrome.

Advantageous Effect

Monoclonal antibodies 77-A5, 77-A6, 90-A3, 90-A9, 90-B2, 90-B7, 90-C4, 90-E5, 90-E6, 90-F1 and 90-F2 according to the present invention have excellent attachment force with respect to a full-length spike protein of MERS-CoV and the S1 domain of the protein, and, of the monoclonal antibodies, the monoclonal antibodies 90-F1, 90-E5, 90-E6, 90-F2, 77-A5 and 77-A6 have excellent attachment force with respect to an RBD antigen of MERS-CoV. Also, the antibodies 77-A5, 77-A6, 90-E5, 90-E6, 90-F1 and 90-F2 exhibit neutralizing capacity with respect to a MERS pseudovirus and MERS-CoV, and the antibodies 90-B2 and 90-B7 exhibit neutralizing capacity only with respect to MERS-CoV. Further, the monoclonal antibodies have a particular monomeric form, and have excellent stability and thus may be useful for treating or diagnosing MERS.

BRIEF DESCRIPTION OF THE DRAWINGS

The application of the preferred embodiments of the present invention is best understood with reference to the accompanying drawings, wherein:

FIG. 5b is a set of graphs illustrating the neutralizing ability of 77-A5, 77-A6, 90-A3, 90-A9, 90-B2, 90-B7, 90-C4, 90-E5, 90-E6, 90-F1, and 90-F2 antibodies against pseudovirus using the spike protein of MERS-CoV Bisha 1 strain.

FIG. 6b is a set of graphs illustrating the neutralizing ability of 90-C4, 90-E5, 90-E6, 90-F1, and 90-F2 antibodies against MERS-CoV.

DESCRIPTION OF THE PREFERRED EMBODIMENTS

Figure 1:
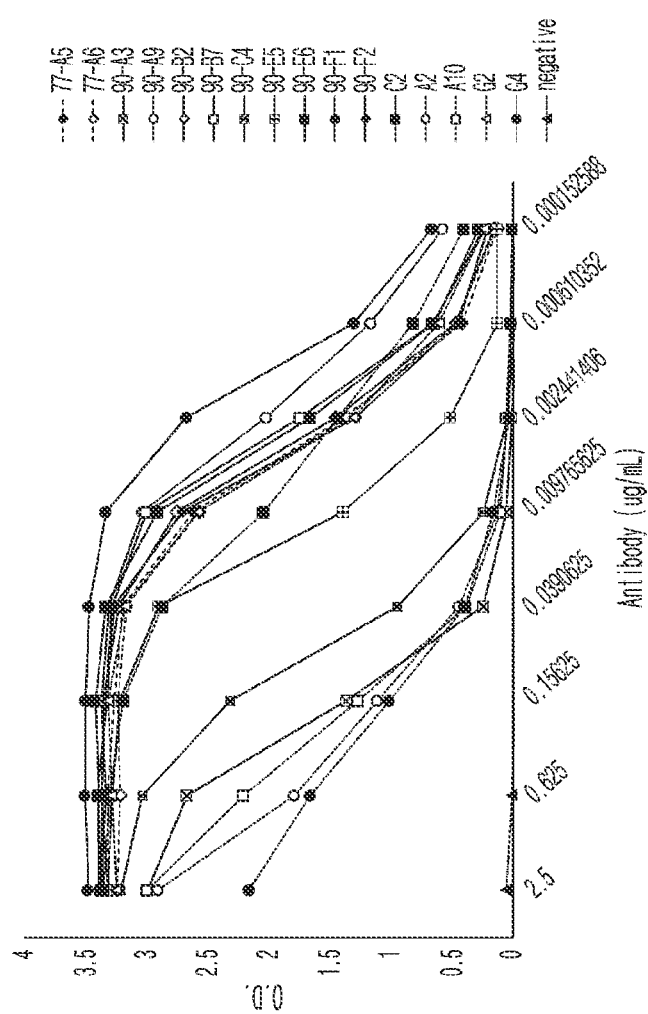
FIG. 1 is a graph illustrating the adhesion of 77-A1, 77-A4, 77-A5, 77-A6, 77-A9, 77-A10, 77-A11, 77-A12, 77-B3, 77-B4, 77-B12, 90-A3, 90-A9, 90-B2, 90-B7, 90-C4, 90-05, 90-D6, 90-E1, 90-E5, 90-E6, 90-F1, and 90-F2 antibodies to the full-length spike trimer antigen of MERS-CoV. Herein, C2, A2, A10, G2, and G4 antibodies developed by NIH, USA, were used as the positive controls.

Hereinafter, the present invention is described in detail.

The present invention provides a heavy chain variable region of the monoclonal antibody binding specifically to the spike protein of MERS-CoV whose complementarity determining region (CDR) is composed of the amino acid sequence represented by SEQ. ID. NO: 1, 3, 5, 7, 9, 11, 13, 15, 17, 19, or NO: 21.

The spike protein above can be a polypeptide composed of any sequence known to those in the art. The polypeptide above can be a variant or a fragment of an amino acid sequence having a different sequence made by deletion, insertion, substitution or combination thereof as long as it does not affect the protein function. The exchange of amino acids in a protein or a peptide, without changing the overall molecular activity, has been well-informed to those in the art. The most common exchanges are between the amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, such modifications as phosphorylation, sulfation, acrylation, glycosylation, methylation, and farnesylation can be occurred. In an example of the present invention, the spike protein can be composed of the amino acid sequence represented by SEQ.ID. NO: 23.

The said heavy chain variable region can specifically bind to the $1^{st}$ to $757^{th}$ amino acid sites from the N-terminus of the spike protein of MERS-CoV. Among the heavy chain variable regions, the heavy chain variable region of the monoclonal antibody whose complementarity determining region is composed of the amino acid sequence represented by SEQ. ID. NO: 1, 3, 15, 17, 19, or NO: 21 can bind specifically to the 377th to 588th amino acid sites from the N-terminus of the spike protein of MERS-CoV.

In a preferred embodiment of the present invention, the present inventors prepared 24 kinds of monoclonal antibodies binding specifically to the spike protein of MERS-CoV. Among them, 77-A5, 77-A6, 90-A3, 90-A9, 90-B2, 90-B7, 90-C4, 90-E5, 90-E6, 90-F1, and 90-F2 antibodies were confirmed to have excellent adhesion to the full-length spike protein and S1 antigen of MERS-CoV (see FIGS. 1 and 2). 90-F1, 90-E5, 90-E6, 90-F2, 77-A5, and 77-A6 antibodies were confirmed to have excellent adhesion to the RBD antigen of MERS-CoV (see FIG. 3).

The present invention also provides a gene encoding the heavy chain variable region of the monoclonal antibody; a recombinant vector containing the gene above; and a host cell introduced with the gene or the recombinant vector above.

The heavy chain variable region above can be characterized by the description above. For example, the heavy chain variable region can be the heavy chain variable region of the monoclonal antibody binding specifically to the spike protein of MERS-CoV whose complementarity determining region (CDR) is composed of the amino acid sequence represented by SEQ. ID. NO: 1, 3, 5, 7, 9, 11, 13, 15, 17, 19, or NO: 21.

The gene above includes not only a sequence encoding the heavy chain variable region but also a polynucleotide having the same nucleotide sequence substantially identical to the gene and a fragment thereof. The polynucleotide having the same nucleotide sequence substantially identical to the gene can have at least 80%, preferably 90%, and more preferably at least 95% homology with the polypeptide of the present invention. As described above, the polynucleotide of the present invention can include a variant in which one or more nucleotide sequences are substituted, deleted or inserted, as long as the variant encode a protein having the equivalent activity.

The said vector is a recombinant vector capable of expressing a target peptide in a desired host cell, which indicates a gene construct containing a necessary regulatory element operably linked thereto in order to express the gene insert. The vector includes such expression regulatory elements as initiation codon, termination codon, promoter, and operator, etc. At this time, the initiation codon and termination codon are generally considered as a part of the nucleotide encoding a polypeptide and they have to be in frame with the coding sequence so as to be functioning in a subject when the gene construct is inserted.

The term "operably linked" herein in this invention indicates a state in which a nucleic acid expression control sequence and a nucleic acid sequence encoding a target protein or RNA are functionally linked to perform a general function. For example, a promoter can be operably linked to a nucleic acid sequence encoding a protein or RNA, which affects the expression of the coding sequence. The operable linkage can be achieved by using the genetic recombination technique which is well-known to those in the art. The site-specific DNA cleavage and linkage can be accomplished by using the enzyme well known to those in the art.

The vector system of the present invention can be constructed through various methods known to those in the art, and a specific method for this is disclosed in "Sambrook, Molecular Cloning, A Laboratory Manual, Cold Spring Harbor Laboratory Press (2001)".

The vector of the present invention can be constructed as a typical cloning vector or an expression vector. Also, the vector of the present invention can be constructed by using a prokaryotic cell or a eukaryotic cell as a host cell. For example, when the vector of the present invention is an expression vector and a prokaryotic cell is used as a host cell, it generally includes a strong promoter capable of promoting transcription (for example, tac promoter, lac promoter, lacUV5 promoter, 1pp promoter, pLζ promoter, pRζ promoter, rac5 promoter, amp promoter, recA promoter, SP6 promoter, trp promoter, and T7 promoter), a ribosome binding site for initiation of translation, and a transcription/translation termination sequence. When *E. coli* (for example, HB101, BL21, DH5a, etc) is used as a host cell, the promoter and operator region of *E. coli* tryptophan biosynthesis pathway (Yanofsky, C., J. Bacteriol., 158:1018-1024 (1984)) and the pL promoter of phage ζ (pLζ promoter, Herskowitz, I. and Hagen, D., Ann. Rev. Genet., 14:399-445(1980)) can be used as a regulatory region. When a *Bacillus* bacterium is used as a host cell, a promoter of a toxin protein gene of *Bacillus thuringiensis* (Appl. Environ. Microbiol. 64:3932-3938(1998); Mol. Gen. Genet. 250:734-741(1996)) or any promoter capable of expressing in *Bacillus* can be used as a regulatory region.

The vector usable in this invention can be constructed by manipulating plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pRSET, pBluescript, pGEX2T, pCR1, pMB9, RP4, and pUC19 etc.), phages (for example, ζgt4.ζB, ζ-Charon, ζEz1, and M13) or viruses (for example, SV40 etc.) frequently used in this field.

When the vector of the invention is an expression vector and the host cell is an eukaryotic cell, a promoter originated from a mammalian cell genome (for example, metallothionine promoter, Y-actin promoter, human hemoglobin promoter, and human muscle creatine promoter) or a promoter originated from a mammalian virus (for example, bovine papulardermatitis virus promoter, adeno-associated virus promoter, vaccinia virus 7.5K promoter, SV40 promoter, cytomegalovirus promoter, HSV tk promoter, mouse mammary tumor virus (MMTV) promoter, HIV LTR promoter, moloney virus promoter, Epstein-Barr virus (EBV) promoter, tobacco mosaic virus promoter, and roas sarcoma virus (RSV) promoter) can be used and a polyadenylation sequence is generally included therein as a transcription termination sequence.

The vectors of the present invention can be fused with other sequences to facilitate the purification of the antibodies expressed therefrom. The sequences adequate for the fusion are exemplified by glutathione S-transferase, maltose binding protein, FLAG, and 6xHis, etc.

Since the protein expressed by the vector of the present invention is an antibody, the expressed antibody can be easily purified through a protein A column without any additional sequence for the purification.

The vector above can also include a selection marker. The selection marker herein is a marker for the selection of a transformed microorganism or a recombinant vector, which can be used to give selectable phenotypes such as drug resistance, nutritional requirements, resistance to cytotoxic agents, or surface protein expression. When a vector containing the selection marker is used, only those cells expressing the selection marker can survive in the selective medium, so that the transformed cells can be easily selected. Any selection marker that can be used in the conventional art can be used. For example, ampicillin, gentamycin, carbenicillin, chloramphenicol, streptomycin, kanamycin, geneticin, neomycin or tetracycline can be used as a selection marker herein.

Various host cells can be used for the expression of the heavy chain variable region of the monoclonal antibody according to the present invention. For example, the host cells can be prokaryotic cells such as *Escherichia* sp., *Bacillus* sp., *Streptomyces* sp., *Pseudomonas* sp., *Proteus* sp., or *Staphylococcus* sp., fungi such as *Aspergillus* sp., yeasts such as *Pichia* sp., *Saccharomyces* sp., *Schizosaccharomyces* sp., or *Neurospora* sp., other lower eukaryotic cells, or eukaryotic sells such as animal cells and plant cells.

As a method of introducing the recombinant vector of the invention into a host cell and transforming it, the conventional gene manipulation method can be used. For example, as a physical method, microinjection, liposome dependent method, direct DNA uptake, receptor-mediated DNA transfer, $Ca^{++}$-directed DNA transfer, or virus-mediated gene transfer can be used.

In a preferred embodiment of the present invention, the present inventors prepared monoclonal antibodies binding specifically to the spike protein of MERS-CoV. Among them, 77-A5, 77-A6, 90-A3, 90-A9, 90-B2, 90-B7, 90-C4, 90-E5, 90-E6, 90-F1, and 90-F2 antibodies were confirmed to have excellent adhesion to the full-length spike protein and S1 antigen of MERS-CoV (see FIGS. 1 and 2). 90-F1, 90-E5, 90-E6, 90-F2, 77-A5, and 77-A6 antibodies were confirmed to have excellent adhesion to the RBD antigen of MERS-CoV (see FIG. 3).

The present invention also provides a composition for the prevention, treatment or diagnosis of Middle East respiratory syndrome comprising the heavy chain variable region of the monoclonal antibody of the invention.

The heavy chain variable region above can be characterized by the description above. For example, the heavy chain variable region can be the heavy chain variable region of the monoclonal antibody binding specifically to the spike protein of MERS-CoV whose complementarity determining region (CDR) is composed of the amino acid sequence represented by SEQ. ID. NO: 1, 3, 5, 7, 9, 11, 13, 15, 17, 19, or NO: 21.

The composition for the treatment of MERS of the present invention can be administered as an independent drug or can be co-administered with other drugs. In the case of co-treatment, it can be administered simultaneously together with the conventional drug or stepwise.

The composition comprising the heavy chain variable region of the monoclonal antibody above can be used for the treatment of virus infection by introducing into a living body in the form of the antibody-drug conjugate. At this time, the drug can be a chemotherapeutic agent, a radionuclide, an immunotherapeutic agent, a cytokine, a chemokine, a toxin, a biological agent, or an enzyme inhibitor. An example of the method to bind an antibiotic to an antibody is explained in the following references: G. Gregoriadies, ed., Academic Press London, (1979); Arnon et al., Recent Results in Cancer Res., 75: 236 (1980); and Moolton et al., Immunolog. Res., 62:47 (1982).

The drug that is preferred for the coupling with the antibody of the present invention include antibiotics, antiparasitic, antifungal, and related agents such as, for example, sulfonamide, penicillin and cephalosporin, aminoglycoside, tetracycline, chloramphenicol, piperazine, chloroquine, diaminopyridine, metroniazide, isoniazid, rifampin, streptomycin, sulfone, erythromycin, polymyxin, nistatin, amphotericin, 5-fluorocytosine, 5-iodo-2'-deoxyuridine, 1-adamanthamine, adenine arabinoside, ammanidin, ribavirin or azatrimidine (AZT). The conditions appropriate and preferred for delivering a drug to a specific target are explained in Trouet et al., Plenum Press, New York and London, 19-30 (1982). The immunoregulator usable as a drug in the form of the antibody-drug conjugate can be a lymphokine or a cytokine, but not always limited thereto.

The composition for the prevention or treatment of MERS of the present invention can include the heavy chain variable region of the monoclonal antibody of the invention as an active ingredient at the concentration of 10-95 weight % by the total weight of the composition. The composition of the present invention can include, in addition to the active ingredient, one or more effective ingredients having the same or similar function to the active ingredient.

The composition for the prevention or treatment of MERS of the present invention can include any generally used carrier, diluent, excipient, or a combination of at least two of those. The pharmaceutically acceptable carrier can be any carrier that is able to deliver the composition of the present invention in a living body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added.

The composition of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules, capsules, and troches. These solid formulations are prepared by mixing the composition of the present invention with one or more suitable excipients such as starch, calcium carbonate, sucrose or lactose, gelatin, etc. Lubricants such as magnesium stearate and talc can also be included therein. Liquid formulations for oral administrations are suspensions, solutions, emulsions and syrups, and the above-mentioned formulations can contain various excipients such as wetting agents, sweeteners, aromatics and preservatives.

Formulations for parenteral administration are sterilized aqueous solutions, water-insoluble excipients, suspensions, and emulsions.

Water insoluble excipients and suspensions can contain propylene glycol, polyethylene glycol, vegetable oil like olive oil, injectable ester like ethylolate, etc.

The composition for the prevention or treatment of MERS of the present invention can be administered orally or parenterally and the parenteral administration includes intraperitoneal injection, intrarectal injection, subcutaneous injection, intravenous injection, intramuscular injection, and intra-thoracic injection.

The composition for the prevention or treatment of MERS of the present invention is administered in a pharmaceutically effective dose. The effective dose can be determined by considering many factors such as the type of disease, severity of the disease, activity of the drug, sensitivity to the drug, administration frequency and pathway, excretion, term of treatment, co-treatment drug and other factors regarded as relevant in the medicinal field. In the case of co-treatment, the composition of the invention can be administered simultaneously together with the other drugs or stepwise.

For the preferred effect, the amount of the active ingredient included in the composition of the present invention can be 0.001~10,000 mg/kg, specifically 0.1~5 g/kg. The administration frequency can be once a day or a few times a day.

The diagnostic composition of the present invention indicates a major tool used for the diagnosis of a target disease, which can include the materials useful for diagnosing MERS-CoV according to the purpose of the invention. The diagnostic method can include the step of contacting an antibody or an antibody fragment with a sample.

The sample herein can be sputum, cells or a tissues taken from nasal cavity, sinus cavity, salivary gland, lung, liver, pancreas, kidney, ear, eye, placenta, digestive tract, heart, ovary, pituitary, adrenal, thyroid, brain or skin, urine, whole blood, serum, plasma, feces, cell culture supernatant, or ruptured eukaryotic cells.

The formation of the sample-antibody conjugate can be detected by colormetric method, electrochemical method, fluorimetric method, luminometry, particle counting method, visual assessment, or scintillation counting method.

The detection is to detect the sample-antibody conjugate, for which various markers can be used. As the marker, an enzyme, a fluorescent material, a ligand, a luminescent material, a microparticle or a radioactive isotope can be used.

The enzyme usable as a detection marker is exemplified by acetylcholinesterase, alkaline phosphatase, γ-D-galactosidase, horseradish peroxidase, and Y-lactamase. The fluorescent material usable as a detection marker can be fluorescein, $Eu^{3+}$, $Eu^{3+}$ chelate, or cryptate. As the ligand, a biotin derivative can be used. As the luminescent material, acridinium ester and an isoluminol derivative can be used. Colloidal gold and colored latex can be used as the microparticle, and $^{57}Co$, $^{3}H$, $^{125}I$, and $^{125}I$-Bonton Hunter reagent can be used as the radioactive isotope.

In a preferred embodiment of the present invention, the present inventors prepared monoclonal antibodies binding specifically to the spike protein of MERS-CoV. Among them, 77-A5, 77-A6, 90-A3, 90-A9, 90-B2, 90-B7, 90-C4, 90-E5, 90-E6, 90-F1, and 90-F2 antibodies were confirmed to have excellent adhesion to the full-length spike protein and S1 antigen of MERS-CoV (see FIGS. 1 and 2). 90-F1, 90-E5, 90-E6, 90-F2, 77-A5, and 77-A6 antibodies were confirmed to have excellent adhesion to the RBD antigen of MERS-CoV (see FIG. 3). 77-A5, 77-A6, 90-E5, 90-E6, 90-F1, and 90-F2 antibodies exhibited neutralizing ability against MERS pseudovirus and MERS-CoV, and 90-B2 and 90-B7 antibodies showed neutralizing ability only against MERS-CoV (see FIGS. 5a, FIG. 5b, FIG. 6a and FIG. 6b). The monoclonal antibodies above were confirmed to be in the form of a certain monomer (see FIG. 7) and have excellent stability (see FIG. 9a to 9c).

The present invention also provides a kit for the detection or quantification of an antigen of Middle East respiratory syndrome by using the antibody and protein comprising the heavy chain variable region of the monoclonal antibody of the invention.

The heavy chain variable region above can be characterized by the description above. For example, the heavy chain variable region can be the heavy chain variable region of the monoclonal antibody binding specifically to the spike protein of MERS-CoV whose complementarity determining region (CDR) is composed of the amino acid sequence represented by SEQ. ID. NO: 1, 3, 5, 7, 9, 11, 13, 15, 17, 19, or NO: 21.

The said kit can be prepared by the conventional method well known to those in the art. The kit can additionally include a buffer, a stabilizer, and an inactive protein. The kit can be used in the following method: fluorescence method performed by detecting fluorescence of the fluorescent material attached as a detection marker to investigate the amount of the detection reagent, high throughput screening (HTS) system through radiation method performed by detecting radiation of the radioactive isotope attached as a detection marker, surface plasmon resonance (SPR) method to measure the surface plasmon resonance change in real time without labeling a detection marker, or surface plasmon resonance imaging (SPRI) method for imaging and verifying SPR system.

In a preferred embodiment of the present invention, the present inventors prepared monoclonal antibodies binding specifically to the spike protein of MERS-CoV. Among them, 77-A5, 77-A6, 90-A3, 90-A9, 90-B2, 90-B7, 90-C4, 90-E5, 90-E6, 90-F1, and 90-F2 antibodies were confirmed to have excellent adhesion to the full-length spike protein and S1 antigen of MERS-CoV (see FIGS. 1 and 2). 90-F1, 90-E5, 90-E6, 90-F2, 77-A5, and 77-A6 antibodies were confirmed to have excellent adhesion to the RBD antigen of MERS-CoV (see FIG. 3). 77-A5, 77-A6, 90-E5, 90-E6, 90-F1, and 90-F2 antibodies exhibited neutralizing ability against MERS pseudovirus and MERS-CoV, and 90-B2 and 90-B7 antibodies showed neutralizing ability only against MERS-CoV (see FIG. 5a, FIG. 5b, FIG. 6a and FIG. 6b). The monoclonal antibodies above were confirmed to be in the form of a certain monomer (see FIG. 7) and have excellent stability (see FIG. 9a to FIG. 9c).

The present invention also provides a method for preventing, treating or diagnosing Middle East respiratory syndrome comprising a step of administering the heavy chain variable region of the monoclonal antibody of the invention to a subject.

The heavy chain variable region above can be characterized by the description above. For example, the heavy chain variable region can be the heavy chain variable region of the monoclonal antibody binding specifically to the spike protein of MERS-CoV whose complementarity determining region (CDR) is composed of the amino acid sequence represented by SEQ. ID. NO: 1, 3, 5, 7, 9, 11, 13, 15, 17, 19, or NO: 21.

In addition, the subject can be a mammal, specifically a human.

The heavy chain variable region of the present invention can be administered orally or parenterally and the parenteral administration includes intraperitoneal injection, intrarectal injection, subcutaneous injection, intravenous injection, intramuscular injection, and intra-thoracic injection.

The heavy chain variable region of the present invention is administered in a pharmaceutically effective dose. The effective dose can be determined by considering many factors such as the type of disease, severity of the disease, activity of the drug, sensitivity to the drug, administration frequency and pathway, excretion, term of treatment, co-treatment drug and other factors regarded as relevant in the medicinal field. In the case of co-treatment, the heavy chain variable region of the invention can be administered simultaneously together with the other drugs or stepwise.

For the preferred effect, the amount of the active ingredient included in the heavy chain variable region of the present invention can be 0.001-10,000 mg/kg, specifically 0.1~5 g/kg. The administration frequency can be once a day or a few times a day.

The heavy chain variable region of the present invention indicates a major tool used for the diagnosis of a target disease, which can include the materials useful for diagnosing MERS-CoV according to the purpose of the invention. The diagnostic method can include the step of contacting an antibody or an antibody fragment with a sample.

The sample herein can be sputum, cells or a tissues taken from nasal cavity, sinus cavity, salivary gland, lung, liver, pancreas, kidney, ear, eye, placenta, digestive tract, heart, ovary, pituitary, adrenal, thyroid, brain or skin, urine, whole blood, serum, plasma, feces, cell culture supernatant, or ruptured eukaryotic cells.

The formation of the sample-antibody conjugate can be detected by colormetric method, electrochemical method, fluorimetric method, luminometry, particle counting method, visual assessment, or scintillation counting method.

The detection is to detect the sample-antibody conjugate, for which various markers can be used. As the marker, an enzyme, a fluorescent material, a ligand, a luminescent material, a microparticle or a radioactive isotope can be used.

The enzyme usable as a detection marker is exemplified by acetylcholinesterase, alkaline phosphatase, γ-D-galactosidase, horseradish peroxidase, and γ-lactamase. The fluorescent material usable as a detection marker can be fluorescein, $Eu^{3+}$, $Eu^{3+}$ chelate, or cryptate. As the ligand, a biotin derivative can be used. As the luminescent material, acridinium ester and an isoluminol derivative can be used. Colloidal gold and colored latex can be used as the microparticle, and $^{57}Co$, $^{3}H$, $^{125}I$, and $^{125}I$-Bonton Hunter reagent can be used as the radioactive isotope.

The present invention also provides a use of the heavy chain variable region of the monoclonal antibody of the invention for the manufacture of a medicament for preventing, treating or diagnosing Middle East respiratory syndrome.

The heavy chain variable region above can be characterized by the description above.

The present invention also provides a light chain variable region of the monoclonal antibody specifically binding to the spike protein of MERS-CoV whose complementarity determining region (CDR) is composed of the amino acid sequence represented by SEQ. ID. NO: 2, 4, 6, 8, 10, 12, 14, 16, 18, 20, or NO: 22.

The spike protein above can be characterized by the description above. In a preferred embodiment of the present invention, the spike protein can be composed of the amino acid sequence represented by SEQ. ID. NO: 23.

The said light chain variable region can specifically bind to the $1^{st}$ to $757^{th}$ amino acid sites from the N-terminus of the spike protein of MERS-CoV. Among the light chain variable regions, the light chain variable region of the monoclonal antibody whose complementarity determining region is composed of the amino acid sequence represented by SEQ. ID. NO: 2, 4, 16, 18, 20, or NO: 22 can bind specifically to the $377^{th}$ to $588^{th}$ amino acid sites from the N-terminus of the spike protein of MERS-CoV.

The present invention also provides a gene encoding the light chain variable region of the monoclonal antibody of the invention; a recombinant vector containing the gene above; and a host cell introduced with the gene or the recombinant vector above.

The light chain variable region above can be characterized by the description above. For example, the light chain variable region can be the light chain variable region of the monoclonal antibody binding specifically to the spike protein of MERS-CoV whose complementarity determining region (CDR) is composed of the amino acid sequence represented by SEQ. ID. NO: 2, 4, 6, 8, 10, 12, 14, 16, 18, 20, or NO: 22.

The gene above is characterized by the description above.

The said vector is a recombinant vector capable of expressing a target peptide in a desired host cell, which indicates a gene construct containing a necessary regulatory element operably linked thereto in order to express the gene insert.

Various host cells can be used in order to express the light chain variable region of the monoclonal antibody according to the present invention. The usable host cells are characterized by the description above.

As a method of introducing the recombinant vector of the invention into a host cell and transforming it, the conventional gene manipulation method can be used. For example, as a physical method, microinjection, liposome dependent method, direct DNA uptake, receptor-mediated DNA transfer, Ca'-directed DNA transfer, or virus-mediated gene transfer can be used.

The present invention also provides a composition for the prevention, treatment or diagnosis of Middle East respiratory syndrome comprising the light chain variable region of the monoclonal antibody of the invention.

The light chain variable region above can be characterized by the description above. For example, the light chain variable region can be the light chain variable region of the monoclonal antibody binding specifically to the spike protein of MERS-CoV whose complementarity determining region (CDR) is composed of the amino acid sequence represented by SEQ. ID. NO: 2, 4, 6, 8, 10, 12, 14, 16, 18, 20, or NO: 22.

The composition for the prevention or treatment of the invention is characterized by the description above.

The diagnostic composition of the present invention indicates a major tool used for the diagnosis of a target disease, which can include the materials useful for diagnosing MERS-CoV according to the purpose of the invention. The diagnostic method can include the step of contacting an antibody or an antibody fragment with a sample. The sample herein can be sputum, cells or a tissues taken from nasal cavity, sinus cavity, salivary gland, lung, liver, pancreas, kidney, ear, eye, placenta, digestive tract, heart, ovary, pituitary, adrenal, thyroid, brain or skin, urine, whole blood, serum, plasma, feces, cell culture supernatant, or ruptured eukaryotic cells.

The present invention also provides a kit for the detection or quantification of an antigen of Middle East respiratory syndrome by using the antibody and protein comprising the light chain variable region of the monoclonal antibody of the invention.

The light chain variable region above can be characterized by the description above. For example, the light chain variable region can be the light chain variable region of the monoclonal antibody binding specifically to the spike protein of MERS-CoV whose complementarity determining region (CDR) is composed of the amino acid sequence represented by SEQ. ID. NO: 2, 4, 6, 8, 10, 12, 14, 16, 18, 20, or NO: 22.

The kit above is characterized by the description above. For example, it can be prepared by the conventional method known to those in the art, and can additionally include a buffer, a stabilizer, and an inactive protein, etc. The kit can be used in the following method: fluorescence method performed by detecting fluorescence of the fluorescent material attached as a detection marker to investigate the amount of the detection reagent, high throughput screening (HTS) system through radiation method performed by detecting radiation of the radioactive isotope attached as a detection marker, surface plasmon resonance (SPR) method to measure the surface plasmon resonance change in real time without labeling a detection marker, or surface plasmon resonance imaging (SPRI) method for imaging and verifying SPR system.

The present invention also provides a method for preventing, treating or diagnosing Middle East respiratory syndrome comprising a step of administering the light chain variable region of the monoclonal antibody of the invention to a subject.

The light chain variable region above can be characterized by the description above. For example, the light chain variable region can be the light chain variable region of the monoclonal antibody binding specifically to the spike protein of MERS-CoV whose complementarity determining region (CDR) is composed of the amino acid sequence represented by SEQ. ID. NO: 2, 4, 6, 8, 10, 12, 14, 16, 18, 20, or NO: 22.

In addition, the subject can be a mammal, specifically a human.

The light chain variable region of the present invention can be administered orally or parenterally and the parenteral administration includes intraperitoneal injection, intrarectal injection, subcutaneous injection, intravenous injection, intramuscular injection, and intra-thoracic injection.

The light chain variable region of the present invention is administered in a pharmaceutically effective dose. The effective dose can be determined by considering many factors such as the type of disease, severity of the disease, activity of the drug, sensitivity to the drug, administration frequency and pathway, excretion, term of treatment, co-treatment drug and other factors regarded as relevant in the medicinal field. In the case of co-treatment, the light chain variable region of the invention can be administered simultaneously together with the other drugs or stepwise.

For the preferred effect, the amount of the active ingredient included in the light chain variable region of the present invention can be 0.001-10,000 mg/kg, specifically 0.1~5 g/kg. The administration frequency can be once a day or a few times a day.

The light chain variable region of the present invention indicates a major tool used for the diagnosis of a target disease, which can include the materials useful for diagnosing MERS-CoV according to the purpose of the invention. The diagnostic method can include the step of contacting an antibody or an antibody fragment with a sample.

The sample herein can be sputum, cells or a tissues taken from nasal cavity, sinus cavity, salivary gland, lung, liver, pancreas, kidney, ear, eye, placenta, digestive tract, heart, ovary, pituitary, adrenal, thyroid, brain or skin, urine, whole blood, serum, plasma, feces, cell culture supernatant, or ruptured eukaryotic cells.

The formation of the sample-antibody conjugate can be detected by colormetric method, electrochemical method, fluorimetric method, luminometry, particle counting method, visual assessment, or scintillation counting method.

The detection is to detect the sample-antibody conjugate, for which various markers can be used. As the marker, an enzyme, a fluorescent material, a ligand, a luminescent material, a microparticle or a radioactive isotope can be used.

The enzyme usable as a detection marker is exemplified by acetylcholinesterase, alkaline phosphatase, γ-D-galactosidase, horseradish peroxidase, and γ-lactamase. The fluorescent material usable as a detection marker can be fluorescein, $Eu^{3+}$, $Eu^{3+}$ chelate, or cryptate. As the ligand, a biotin derivative can be used. As the luminescent material, acridinium ester and an isoluminol derivative can be used. Colloidal gold and colored latex can be used as the microparticle, and $^{57}Co$, $^{3}H$, $^{125}I$, and $^{125}I$-Bonton Hunter reagent can be used as the radioactive isotope.

The present invention also provides a use of the light chain variable region of the monoclonal antibody of the invention for the manufacture of a medicament for preventing, treating or diagnosing Middle East respiratory syndrome.

The light chain variable region above can be characterized by the description above.

The present invention also provides a monoclonal antibody specifically binding to the spike protein of MERS-CoV containing a heavy chain variable region whose complementarity determining region is composed of the amino acid sequence represented by SEQ. ID. NO: 1, 3, 5, 7, 9, 11, 13, 15, 17, 19, or NO: 21, and a light chain variable region whose complementarity determining region is composed of the amino acid sequence represented by SEQ. ID. NO: 2, 4, 6, 8, 10, 12, 14, 16, 18, 20, or NO: 22.

The spike protein above can be characterized by the description above. In a preferred embodiment of the present invention, the spike protein can be composed of the amino acid sequence represented by SEQ. ID. NO: 23. The light chain variable region and the heavy chain variable region can be characterized by the description above.

The monoclonal antibody is an antibody produced by a single antibody-forming cell, which has a uniform primary structure (amino acid sequence). The monoclonal antibody recognizes only one antigenic determinant and is generally produced by culturing the hybridoma cells prepared by the fusion of cancer cells and antibody producing cells. This antibody also can be produced by using other recombinant protein expressing host cells using the obtained antibody gene sequence.

The present invention also provides a gene encoding the monoclonal antibody of the invention; a recombinant vector containing the gene above; and a host cell introduced with the gene or the recombinant vector above.

The monoclonal antibody above can be characterized by the description above. For example, the monoclonal antibody can be the antibody binding specifically to the spike protein of MERS-CoV containing a heavy chain variable region whose complementarity determining region is composed of the amino acid sequence represented by SEQ. ID. NO: 1, 3, 5, 7, 9, 11, 13, 15, 17, 19, or NO: 21, and a light chain variable region whose complementarity determining region is composed of the amino acid sequence represented by SEQ. ID. NO: 2, 4, 6, 8, 10, 12, 14, 16, 18, 20, or NO: 22.

The gene above is characterized by the description above.

The said vector is a recombinant vector capable of expressing a target peptide in a desired host cell, which indicates a gene construct containing a necessary regulatory element operably linked thereto in order to express the gene insert.

Various host cells can be used in order to express the monoclonal antibody according to the present invention. The usable host cells are characterized by the description above.

As a method of introducing the recombinant vector of the invention into a host cell and transforming it, the conventional gene manipulation method can be used. For example, as a physical method, microinjection, liposome dependent method, direct DNA uptake, receptor-mediated DNA transfer, Ca'-directed DNA transfer, or virus-mediated gene transfer can be used.

The present invention also provides a composition for the prevention, treatment or diagnosis of Middle East respiratory syndrome comprising the monoclonal antibody of the invention.

The monoclonal antibody above can be characterized by the description above. For example, the monoclonal antibody can be the antibody binding specifically to the spike protein of MERS-CoV containing a heavy chain variable region whose complementarity determining region is composed of the amino acid sequence represented by SEQ. ID. NO: 1, 3, 5, 7, 9, 11, 13, 15, 17, 19, or NO: 21, and a light chain variable region whose complementarity determining region is composed of the amino acid sequence represented by SEQ. ID. NO: 2, 4, 6, 8, 10, 12, 14, 16, 18, 20, or NO: 22.

The composition for the prevention or treatment of the invention is characterized by the description above.

The diagnostic composition of the present invention indicates a major tool used for the diagnosis of a target disease, which can include the materials useful for diagnosing MERS-CoV according to the purpose of the invention. The diagnostic method can include the step of contacting an antibody or an antibody fragment with a sample. The sample herein can be sputum, cells or a tissues taken from nasal cavity, sinus cavity, salivary gland, lung, liver, pancreas, kidney, ear, eye, placenta, digestive tract, heart, ovary, pituitary, adrenal, thyroid, brain or skin, urine, whole blood, serum, plasma, feces, cell culture supernatant, or ruptured eukaryotic cells.

The present invention also provides a kit for the detection or quantification of an antigen of Middle East respiratory syndrome comprising the monoclonal antibody of the invention.

The monoclonal antibody above can be characterized by the description above. For example, the monoclonal antibody can be the antibody binding specifically to the spike protein of MERS-CoV containing a heavy chain variable region whose complementarity determining region is composed of the amino acid sequence represented by SEQ. ID. NO: 1, 3, 5, 7, 9, 11, 13, 15, 17, 19, or NO: 21, and a light chain variable region whose complementarity determining region is composed of the amino acid sequence represented by SEQ. ID. NO: 2, 4, 6, 8, 10, 12, 14, 16, 18, 20, or NO: 22.

The kit above is characterized by the description above. For example, it can be prepared by the conventional method known to those in the art, and can additionally include a buffer, a stabilizer, and an inactive protein, etc. The kit can be used in the following method: fluorescence method performed by detecting fluorescence of the fluorescent material attached as a detection marker to investigate the amount of the detection reagent, high throughput screening (HTS) system through radiation method performed by detecting radiation of the radioactive isotope attached as a detection marker, surface plasmon resonance (SPR) method to measure the surface plasmon resonance change in real time without labeling a detection marker, or surface plasmon resonance imaging (SPRI) method for imaging and verifying SPR system.

The present invention also provides a method for preventing, treating or diagnosing Middle East respiratory syndrome comprising a step of administering the monoclonal antibody of the invention to a subject.

The monoclonal antibody above can be characterized by the description above. For example, the monoclonal antibody can be the antibody binding specifically to the spike protein of MERS-CoV containing a heavy chain variable region whose complementarity determining region is composed of the amino acid sequence represented by SEQ. ID. NO: 1, 3, 5, 7, 9, 11, 13, 15, 17, 19, or NO: 21, and a light chain variable region whose complementarity determining region is composed of the amino acid sequence represented by SEQ. ID. NO: 2, 4, 6, 8, 10, 12, 14, 16, 18, 20, or NO: 22.

In addition, the subject can be a mammal, specifically a human.

The monoclonal antibody of the present invention can be administered orally or parenterally and the parenteral administration includes intraperitoneal injection, intrarectal injection, subcutaneous injection, intravenous injection, intramuscular injection, and intra-thoracic injection.

The monoclonal antibody of the present invention is administered in a pharmaceutically effective dose. The effective dose can be determined by considering many factors such as the type of disease, severity of the disease, activity of the drug, sensitivity to the drug, administration frequency and pathway, excretion, term of treatment, co-treatment drug and other factors regarded as relevant in the medicinal field. In the case of co-treatment, The monoclonal antibody of the invention can be administered simultaneously together with the other drugs or stepwise.

For the preferred effect, the amount of the active ingredient included in the monoclonal antibody of the present invention can be 0.001-10,000 mg/kg, specifically 0.1~5 g/kg. The administration frequency can be once a day or a few times a day.

The monoclonal antibody of the present invention indicates a major tool used for the diagnosis of a target disease, which can include the materials useful for diagnosing MERS-CoV according to the purpose of the invention. The diagnostic method can include the step of contacting an antibody or an antibody fragment with a sample.

The sample herein can be sputum, cells or a tissues taken from nasal cavity, sinus cavity, salivary gland, lung, liver, pancreas, kidney, ear, eye, placenta, digestive tract, heart, ovary, pituitary, adrenal, thyroid, brain or skin, urine, whole blood, serum, plasma, feces, cell culture supernatant, or ruptured eukaryotic cells.

The formation of the sample-antibody conjugate can be detected by colormetric method, electrochemical method, fluorimetric method, luminometry, particle counting method, visual assessment, or scintillation counting method.

The detection is to detect the sample-antibody conjugate, for which various markers can be used. As the marker, an enzyme, a fluorescent material, a ligand, a luminescent material, a microparticle or a radioactive isotope can be used.

The enzyme usable as a detection marker is exemplified by acetylcholinesterase, alkaline phosphatase, γ-D-galactosidase, horseradish peroxidase, and γ-lactamase. The fluorescent material usable as a detection marker can be fluorescein, $Eu^{3+}$, $Eu^{3+}$ chelate, or cryptate. As the ligand, a biotin derivative can be used. As the luminescent material, acridinium ester and an isoluminol derivative can be used. Colloidal gold and colored latex can be used as the microparticle, and $^{57}Co$, $^{3}H$, $^{125}I$, and $^{125}I$-Bonton Hunter reagent can be used as the radioactive isotope.

The present invention also provides a use of the monoclonal antibody of the invention for the manufacture of a medicament for preventing, treating or diagnosing Middle East respiratory syndrome.

The monoclonal antibody above can be characterized by the description above.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Monoclonal Antibody Binding Specifically to MERS-CoV Spike Protein In the period between May and July 2015 when MERS occurred in Korea, blood samples were taken from patients with early stage MERS. Peripheral blood mononuclear cells (PBMCs) were isolated from those blood samples by the conventional method, which were cryopreserved. B cells having MERS antibody were separated as single cells (single cell sorting) from the PBMCs isolated by FACS using the MERS-CoV spike trimer protein probe (PE fluorescent dye), anti-human IgG-FITC and anti-human CD20 IgG-Cy55PerCP, provided by NIH/NIAID/VRC, USA. Unnecessary immune cells except B cells were negatively selected by attaching CD3, CD4, CD8 and CD14 markers and removed by FACS. CDR regions of the heavy chain, kappa light chain and lambda light chain of the antibody gene separated from the B cells obtained from patients with early phase MERS were amplified by PCR, and the sequences were confirmed. The nucleotide sequence appropriate for the immunoglobulin antibody expression was examined by using a web-based IMGT (International Immunogenetics Information systems, http://www.imgt.org) program. CDR regions of the heavy chain, kappa light chain and lambda light chain of the antibody were cloned in pVRC vector comprising mouse IgM signal peptide and IgG constant region provided by NIH/NIAID/VRC, USA. Then, Expi293F cells were transfected with the prepared antibody plasmid. 5 days later, the cell culture fluid was obtained, from which the antibody was prepared by purifying with protein G agarose column.

Experimental Example 1: Investigation of Antibody Adhesion to Antigen

<1-1> Investigation of Antibody Adhesion to MERS-CoV Full-Length Spike Protein Trimer Antigen The binding affinity of 24 kinds of the antibodies prepared in Example 1 to the full-length spike trimer antigen of MERS-CoV, which is composed of amino acids 1 to 1275 from the N-terminus of the spike protein and is lack of the transmembrane region, was confirmed. The adhesion was compared among the monoclonal antibodies prepared in Example 1, the human anti-S1 monoclonal antibodies A2 and A10, the human anti-RBD monoclonal antibody C2, the mouse anti-S2 monoclonal antibody G4, and the mouse anti-S1 monoclonal antibody G2, developed by NIH, USA.

Particularly, MERS-CoV full spike trimer antigen was loaded in MaxiSorp 96-well plate (Nunc) at the concentration of 0.2 μg/100 μl PBS/well, followed by reaction at 4° C. for a day. Upon completion of the reaction, the reaction solution was eliminated, followed by blocking with a blocking solution containing 5% skim milk and 2% BSA in PBST at room temperature for 1 hour. Next, the antibody prepared in Example 1 was diluted in the blocking solution at the concentration of 10, 2.5, 0.625, 0.15625, 0.039, 0.009, 0.002, 0.0006, or 0.0001 μg/ml, which was loaded in the plate coated with the full spike trimer antigen above, followed by reaction at room temperature for 1 hour. The plate was washed with PBST 6 times, to which rabbit anti-human IgG H&L-HRP (horse radish peroxidase) secondary antibody was added, followed by reaction for 1 hour. Anti-mouse IgG-HRP secondary antibody was added to the well containing G2 and G4 antibodies, followed by reaction for 1 hour. After washing with PBST 6 times, 100 μl of TMB solution was added to each well, followed by reaction at room temperature for 30 minutes with blocking light. Upon completion of the reaction, 100 μl of stop solution (Enzygost) was added to each well. Then, $OD_{450}$ was measured to investigate the antibody adhesion to antigen.

TABLE 1

CDR amino acid sequences to 11 MERS antibodies

| Antibody | CDR sequence of heavy chain | CDR sequence of kappa light chain | CDR sequence of lambda light chain |
|---|---|---|---|
| 77-A5 | TGVHSQVQLVQSGAEVKKP GSSVKVSCKASGGTFRSHAI SWVRQAPGQGLEWMGGIIPI FASANYAQKFQGRVTITAD ESTSTAYMDLSSLRSDDTAV YYCAKNVSPKSYSGRYSISY FYGVDVWGQGTTVTVSSA (SEQ. ID. NO: 1) | | TGSWAQSALTQPPSASGTP GQRVTISCSGSSSNIGSNTV NWYQQLPGTAPKLLIYSNN QRPSGVPDRFSGSKSGTSAS LAISGLQSEDEADYYCAAW DDSLSGHYVFGTGTKVTVL GQPKANPTVTLFPPS (SEQ. ID. NO: 2) |
| 77-A6 | TGVHSEVQLLESGGGLVQP GGSLRLSCADSGLTFSSYAM SWVRQAPGKGLEWVSAISV SGGSTYYSDSVKGRFTISRD NSKNTLSLQMNSLRAEDTA VYYCVKARSIVGPFDYWGQ GTLVTVSSAS (SEQ. ID. NO: 3) | | TGSWAQSALTQPPSVSAAP GQKVTISCSGSSSNIGNNYV SWYQHLPGTAPKLLIYDNI MRPSGIPDRFSGSKSGTSAT LGITGLQTGDEADYYCGTW DTSLSAVVFGGGTKLTVLG QPKAAPSVTLFPPS (SEQ. ID. NO: 4) |
| 90-A3 | TGVHSQVQLVQSGAEVKKP GASVKVSCMTSGYTFTSYGI SWVRQAPGQGLEWMGWIS AYNGNTNYAQKLQGRVTM TTDTSTSTAYMELRSLRSDD TAVYYCARDRGAYWDCGG DCYLSAFDYWGQGTLVTVS SAS (SEQ. ID. NO: 5) | | TGSNSQAVVTQPPSVSAAP GQKVTISCSGSSSNIGNNYV SWYQQLPGTAPKLLIYDNN KRPSGIPDRFSGSKSGTSAT LGITGLQTGDEADYYCGTW DSSLSAVVFGGGTKLTVLG QPKAAPSVTLFPPS (SEQ. ID. NO: 6) |
| 90-A9 | TGVHSQVQLVQSGAEVKKP GSSVKVSCKASGGTFSSFPIS WVRQAPGQGLEWMGGIIPIF GAANYAQKFQGRVTITAD STSTAYMELSSLRSEDTAVY YCARNYEEIVVIPAIMNFGY WGQGTLVTVSSAS (SEQ. ID. NO: 7) | TGVHSEIVLTQSPGTLSL SPGERATLSCRASQSVA SSYLAWYQQKPGQAPR LLIYGTSSRATGIPDRFS GSGSGADFTLTISRLEPE DFAVYYCQQYGTSPLT FGGGTKVEIK (SEQ. ID. NO: 8) | |
| 90-B2 | TGVHSQVQLQESGPGLVKP SETLSLTCTVSGGSISSSSYY WGWIRQPPGKGLEWIGSIY YSGNTYYNPSLKSRVTISVD TSKNHFSLRLSSVTAADTAV YFCARSLPHYDSTGYLLYW GQGTLVTVSSAS (SEQ. ID. NO: 9) | TGVHSEIVLTQSPATLSL SPGGRATLSCRASQSVS RYLAWYQQKPGRAPRL LIYDASNRAPGIPARFSG SGSGTDFTLTISSLEPED FAVYYCQQRSNWPQTT FGPGTKVDIKRT (SEQ. ID. NO: 10) | |
| 90-B7 | TGVHSEVQLLESGGGLVKP GGSLRLSCAASGFTFGSYSM TWVRQAPGKGLEWVSSISSS SSYIYYADSVKGRFTISRDN AKNSLFLQMNSLRAEDTAV YYCARGNGYCSHNSCYKIG VWFDPWGQGTLVTVSSAS (SEQ. ID. NO: 11) | | TGSNSQAVVTQPPSVSAAP GQKVTISCSGSSSNIGNNYV SWYQQLPGTAPKLLIYDNN KRPSGIPDRFSGSKSGTSAT LGITGLQTGDEADYYCGTW DSSLSAFVFGTGTKVTVLG QPKANPTVTLFPPS (SEQ. ID. NO: 12) |
| 90-C4 | TGVHSQVQLQESGPGLVKP SGTLSLTCAVSGGSINSSNW WSWVRQPPGKGLEWIGEIY YSGSTNYNPSLKSRVTTSVD NSKNQFSLKLSSVTAADTA VYYCATFDSGGYNPNWFDP WGQGTLVTVSSAS (SEQ. ID. NO: 13) | | TGSWAQSALTQPPSVSGAP GQRVTISCTGSSSSIGAGYD VHWYQQLPGTAPKLLIYGN SNRPSGVPDRFSGSKSGTSA SLAITGLQAEDEADYYCQS YDSSLSGYVFGTGTKVTVL GQPKANPTVTLFPPS (SEQ. ID. NO: 14) |

TABLE 1-continued

CDR amino acid sequences to 11 MERS antibodies

| Antibody | CDR sequence of heavy chain | CDR sequence of kappa light chain | CDR sequence of lambda light chain |
|---|---|---|---|
| 90-E5 | TGVHSQVQLVQSGAEVKKP GSSVKVSCKASGGTFSSYTI NWVRQAPGQGLEWMGGIIP IFGTANYAQKFQGRVTITAD ASTSTAYMELSSLRSEDTAV YYCARVLLRSSSWFSSNWF DPWGQGTLVTVSSAS (SEQ. ID. NO: 15) | | TGSWAQSVLTQPPSVSGAP GQRVTISCTGSSSNIGAGYD VHWYQQLPGTAPKVLIYG NSNRPSGVPDRFSGSKSDTS ASLAITGLQAEDEADYYCQ SYDSSLSVVFGGGTKLTVL GQPKAAPSVTLFPPS (SEQ. ID. NO: 16) |
| 90-E6 | TGVHSEVQLVESGGGLVQP GRSLRLSCAASGFTFDDHA MHWVRQAPGKGLEWVSGF SWNSGSIGYADSVKGRFTIS RDNAKNSLYLQMNSLRAED TALYYCAKDRRSDYYFYG MDVWGQGTTVTVSSAS (SEQ. ID. NO: 17) | | TGSWAQSVLTQPPSVSAAP GQKVTISCSGSRSNIGNNYV SWYQQLPGTAPKLLIYDNN KRPSGIPDRFSGSKSGTSAT LGITGLQTGDEADYYCGTW DSSLNAGVFGGGTKLTVLG QPKAAPSVTLFPPS (SEQ. ID. NO: 18) |
| 90-F1 | TGVHSQVQLVQSGAEVKRP GSSVKVSCKTSGGTFNNNAI NWVRQAPGQGLEWMGGIIP FFGIAKYAQKFQGRVTITAD ESTSTAYMELSSLRSEDTAV YYCARDLPRESSYGSGSYYT HYYAMDVWGQGTTVTVSS AS (SEQ. ID. NO: 19) | TGVHSEIVLTQSPATLSL SPGERATLSCGASQSVS SSYLAWYQQKPGLAPR LLIYDASSRATGIPDRFS GSGSGTDFTLTISRLEPE DFAVYYCQQYGSSPLTF GGGTKVEIKRT (SEQ. ID. NO: 20) | |
| 90-F2 | TGVHSQVQLVQSGAEVKKP GASVKVSCKASGYTFTTYY MHWVRQAPGQGLEWMGII NPSGGSTSYAQKFQGRVTM TRDTSTSTVYMELSSLRSED TAVYYCARGAVVVILDYW GQGTLVTVSSAS (SEQ. ID. NO: 21) | TGVHSDIQMTQSPSTLS ASVGDRVTITCRASQTI STWLAWYQQKPGKAP KLLIYKASSLESGVPSRF SGSGSGTEFTLTISSLQP DDFATYYCQQYNSYSY TFGQGTKLEIKRT (SEQ. ID. NO: 22) | |

As a result, as shown in FIG. 1, among the 24 antibodies, 77-A5, 77-A6, 90-A3, 90-A9, 90-B2, 90-B7, 90-C4, 90-E5, 90-E6, 90-F1, and 90-F2 antibodies demonstrated excellent adhesion to MERS-CoV full spike trimer antigen, which was greater than that of A2, A10, and G4 antibodies (FIG. 1). CDR sequences of 11 kinds of the antibodies demonstrating excellent adhesion to the full spike trimer antigen are shown in Table 1.

<1-2> Investigation of Antibody Adhesion to MERS-CoV S1 Antigen

The binding affinity of 24 kinds of the antibodies prepared in Example 1 was investigated by the same manner as described in Experimental Example 1-1 except that the MERS-CoV S1 domain composed of amino acids 1 to 757 from the N-terminus of the spike protein was used as an antigen.

Figure 2:
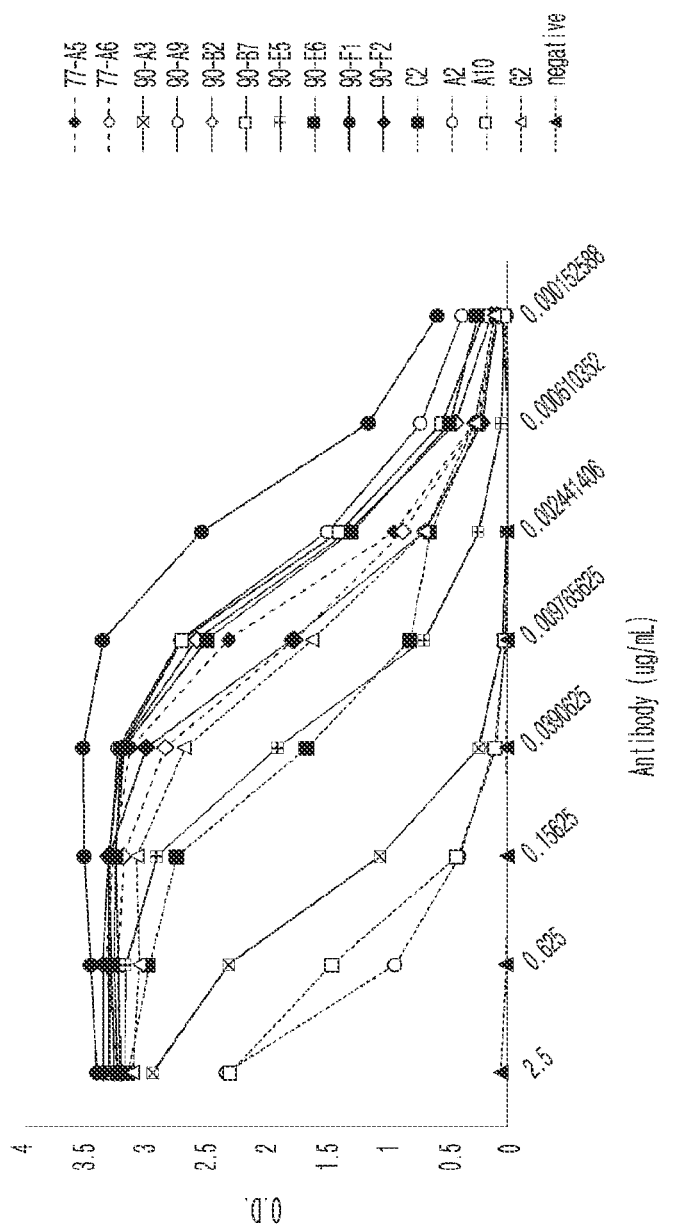
FIG. 2 is a graph illustrating the adhesion of the antibodies above to the MERS-CoV S1 antigen composed of the amino acids 1 to 757 of the spike protein.

As a result, as shown in FIG. 2, among the 24 antibodies, 77-A5, 77-A6, 90-A3, 90-A9, 90-B2, 90-B7, 90-C4, 90-E5, 90-E6, 90-F1, and 90-F2 antibodies demonstrated excellent adhesion to the S1 antigen, which was greater than that of the A2 and A10 antibodies developed by NIH, USA. In particular, 90-F1, 90-B7, 90-E6, 77-A4, 77-A5, 90-F2, and 77-A6 antibodies demonstrated higher adhesion than that of C2 and G2 antibodies (FIG. 2).

<1-3> Investigation of antibody adhesion to MERS-CoV RBD antigen

The binding affinity of 24 kinds of the antibodies prepared in Example 1 was investigated by the same manner as described in Experimental Example 1-1 except that the MERS-CoV RBD (receptor binding domain) composed of amino acids 377 to 588 from the N-terminus of the spike protein was used as an antigen.

Figure 3:
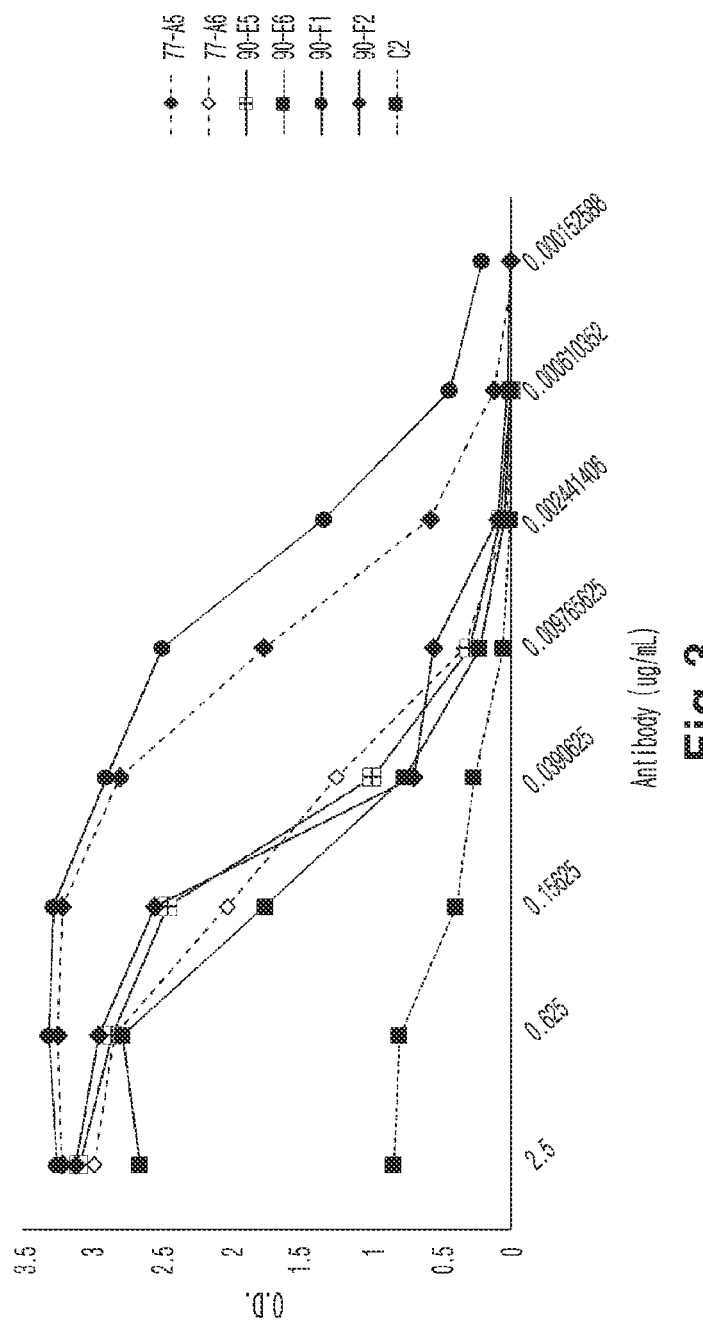
FIG. 3 is a graph illustrating the adhesion of the antibodies above to the MERS-CoV RBD antigen composed of the amino acids 377 to 588 of the spike protein.

As a result, as shown in FIG. 3, among those 24 antibodies, 90-F1, 90-E5, 90-E6, 90-F2, 77-A5, and 77-A6 antibodies showed higher adhesion to the RBD antigen than that of C2 antibody. The rest of those antibodies did not show adhesion to the RBD antigen (FIG. 3).

<1-4> Investigation of antibody adhesion to MERS-CoV S2 antigen

The binding affinity of 24 kinds of the antibodies prepared in Example 1 was investigated by the same manner as described in Experimental Example 1-1 except that the MERS-CoV S2 domain composed of amino acids 757 to 1275 from the N-terminus of the spike protein was used as an antigen.

Figure 4:
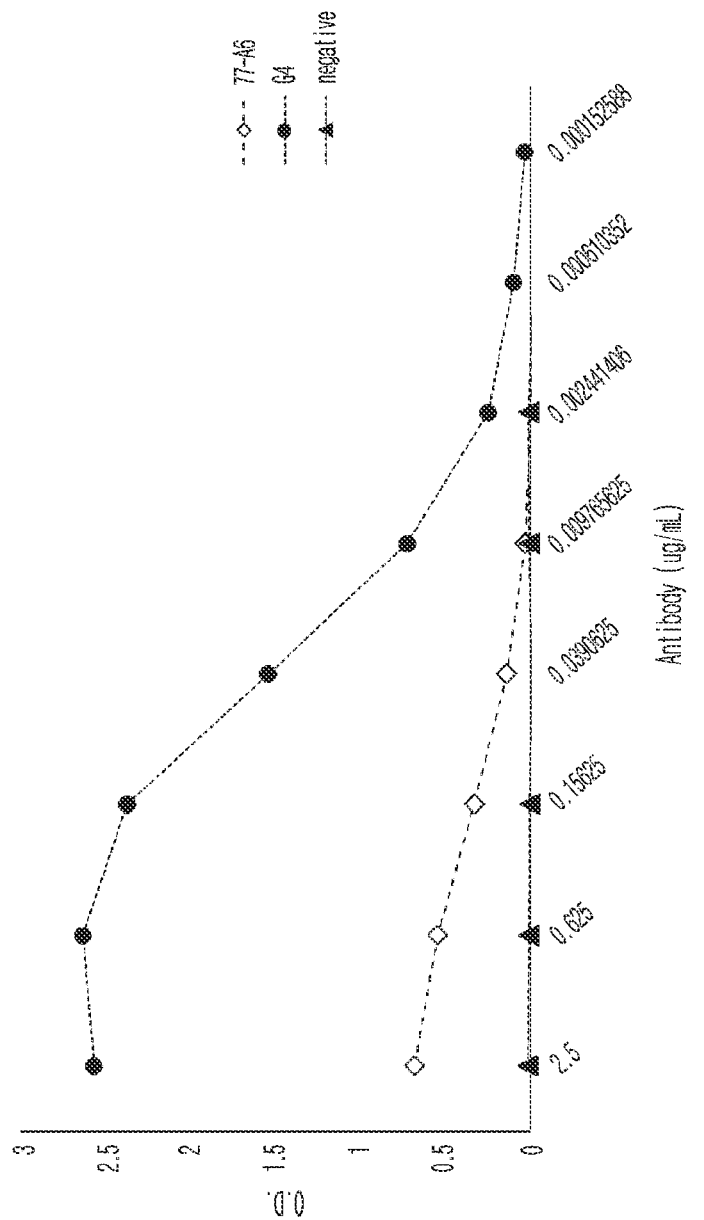
FIG. 4 is a graph illustrating the adhesion of the antibodies above to the MERS-CoV S2 antigen composed of the amino acids 757 to 1275 of the spike protein.

As a result, as shown in FIG. 4, all of those 24 antibodies prepared in Example 1 showed very low adhesion to the S2 antigen (FIG. 4).

Experimental Example 2: Investigation of Neutralizing Capacity of Antibody Against MERS Pseudovirus Huh7.5 cell line was treated with trypsin and suspended. The cells were diluted with DMEM (Dulbecco's modified Eagle's medium) containing 10% FBS, which were distributed in a 96-well tissue culture plate at the density of $10^4$ cells/100 µl/well, followed by culture for a day. In the meantime, 90 µl of the supernatant of recombinant lentivirus (recombinant MRES pseudovirus expressing luciferase, NIH/NIAID/VRC, USA) containing MERS-CoV spike protein (Erasmus strain or Bisha 1 strain) and 90 µl of the antibody of Example 1 diluted in cell culture medium at the concentration of 10, 1, 0.1, 0.01, or 0,001 µs/ml were mixed with DMEM containing 10% FBS, followed by reaction at 37° C. for 45 minutes, resulting in the preparation of a reaction mixture. The mixture was added to the culture plate (50 µl/well), to which DMEM containing 10% FBS was added (100 µl/well), followed by culture in a 37° C., 5% $CO_2$ incubator for 3 days. After discarding the culture fluid, 1× lysis buffer (Promega, E153A) was added therein at the concentration of 25 µl/well, followed by stirring for 15 minutes to lyse the cells. The lysed cells were added with luciferase substrate reagent (Promega, E151A) (50 µl/well). Fluorescence was measured with a luminometer and neutralizing capacity was calculated by the following mathematical formula 1.

Neutralizing Capacity (%)=100−(luciferase signal mean value of antibody-treated pseudovirus/ background signal of antibody-non-treated pseudovirus×100)  [Mathematical Formula 1]

TABLE 2

Neutralizing capacity of 11 antibodies

| Antibody Conc. (µg/ml) | Neutralizing Capacity (%) | | | | |
|---|---|---|---|---|---|
| | 77-A5 | 77-A6 | 90-A3 | 90-A9 | 90-B2 |
| 10 | 95.93 | 99.04 | −29.25 | −9.72 | −152.78 |
| 2.5 | 92.87 | 99.53 | 5.01 | 31.92 | −71.75 |
| 0.625 | 67.05 | 97.96 | 22.00 | 18.73 | −59.75 |
| 0.15625 | 64.10 | 92.04 | 28.44 | 15.01 | −59.65 |
| 0.039063 | 3.16 | 56.75 | 2.43 | −6.41 | −40.74 |
| 0.009766 | 28.89 | 41.59 | −15.18 | −1.78 | −44.11 |
| 0.002441 | −3.78 | 3.81 | 6.57 | −18.34 | −25.61 |
| Virus alone | 0.00 | 0.00 | | 0.00 | 0.00 |

| Antibody Conc. (µg/ml) | Neutralizing Capacity (%) | | | | | |
|---|---|---|---|---|---|---|
| | 90-B7 | 90-C4 | 90-E5 | 90-E6 | 90-F1 | 90-F2 |
| 10 | −49.92 | 20.88 | 91.00 | 58.10 | 99.83 | 98.17 |
| 2.5 | −9.19 | 28.48 | 79.40 | 66.30 | 99.65 | 94.39 |
| 0.625 | −32.26 | −3.31 | 61.12 | 44.77 | 98.55 | 86.01 |
| 0.15625 | −30.39 | 17.46 | 46.94 | 41.31 | 98.56 | 59.63 |
| 0.039063 | −21.07 | 2.43 | 38.62 | 41.83 | 88.45 | 48.10 |
| 0.009766 | 0.10 | −23.37 | 37.07 | 10.61 | 69.87 | 21.76 |
| 0.002441 | −9.71 | −7.53 | 38.20 | 36.45 | 54.92 | 48.40 |
| Virus alone | 0.00 | 0.00 | 15.11 | 26.03 | 0.00 | 0.00 |

Figure 5A:
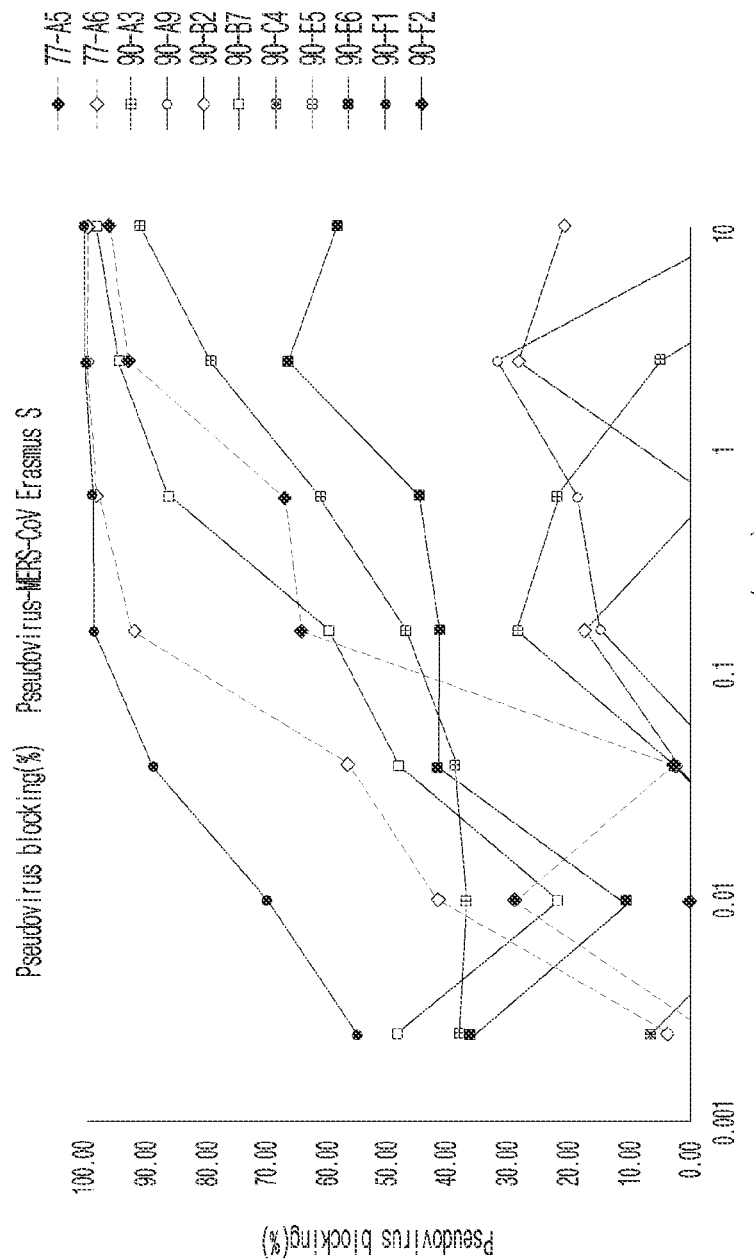
FIG. 5a is a set of graphs illustrating the neutralizing ability of 77-A5, 77-A6, 90-A3, 90-A9, 90-B2, 90-B7, 90-C4, 90-E5, 90-E6, 90-F1, and 90-F2 antibodies against pseudovirus using the spike protein of MERS-CoV Erasmus strain.

As a result, as shown in FIG. 5a, FIG. 5b and Table 2, 77-A5, 77-A6, 90-E5, 90-E6, 90-F1, and 90-F2 antibodies demonstrated neutralizing capacity against MERS pseudovirus Erasmus strain. Among them, 77-A5, 77-A6, 90-F1, and 90-F2 antibodies showed neutralizing capacity against MERS pseudovirus Bisha 1 strain as well. 90-F1 antibody displayed the highest neutralizing capacity against MERS pseudovirus Erasmus strain and Bisha 1 strain (FIG. 5a, FIG. 5b and Table 2). Therefore, it was confirmed that 77-A5, 77-A6, 90-F1, and 90-F2 antibodies had a wide range of neutralizing capacity.

Experimental Example 3: Investigation of Neutralizing Capacity of Antibody Against MERS-CoV To investigate neutralizing capacity of the antibodies prepared in Example 1, plaque reduction neutralizing test (PRNT) was performed with MERS-CoV (Erasmus strain and KNIH strain). First, Vero cells were distributed in a 24-well plate at the density of $10^5$ cells/well, followed by culture. The culture medium was discarded therefrom. The antibodies of Example 1 diluted in cell culture medium at the concentration of 10, 2.5, 0.625, 0.156, 0.039, 0.009, or 0.002 ng/ml were mixed with the MERS-CoV (EMC, KNIH-002, KNIH-016, and KNIH-042 strains) diluted in 50 PFU/well, resulting in the preparation of a mixed solution. The mixed solution was added to the culture plate at the concentration of 100 µl/well, followed by reaction at 37° C. for 1 hour. Then, DMEM containing 1.5% CMC (carboxymethyl cellulose) was added to the plate at the concentration of 1 ml/well, followed by culture for 3 days. Upon completion of the culture, plaques were observed by crystal violet staining. The number of plaques in each well was calculated, based on which neutralizing capacity was calculated by the following mathematical formula 2. $ND_{50}$ was also calculated by the following mathematical formula 3 to calculate the neutralizing capacity. In the mathematical formula 3, m indicates a $log_{10}$ value of the highest rate of dilution, Δ indicates a constant interval between the rates of dilution expressed by a $log_{10}$ value, and Σp indicates the average number of plaques for sum of all ratios of plaques/virus control.

Neutralizing Capacity (%)=100−(plaque number of antibody-treated MERS virus/plaque number of antibody-non-treated MERS virus×100)  [Mathematical Formula 2]

$log_{10}^{ND_{50}} = m - \Delta(\Sigma p - 0.5)$  [Mathematical Formula 3]

TABLE 3

Neutralizing capacity of antibodies analyzed by PRNT

| Antibody | $ND_{50}$ | $ND_{50}$ antibody conc. (µg/ml) |
|---|---|---|
| 77-A5 | 35.60 | 0.28 |
| 77-A6 | 95.73 | 0.10 |
| 90-A3 | 0.63 | 15.81 |
| 90-A9 | 0.58 | 17.30 |
| 90-B2 | 39.52 | 0.25 |
| 90-B7 | 14.93 | 0.67 |
| 90-C4 | 0.78 | 12.76 |
| 90-E5 | 6.60 | 1.51 |
| 90-E6 | 0.68 | 14.78 |
| 90-F1 | 956.46 | 0.01 |
| 90-F2 | 53.96 | 0.19 |
| Negative Control | 1.00 | 10.04 |

Figure 6A:
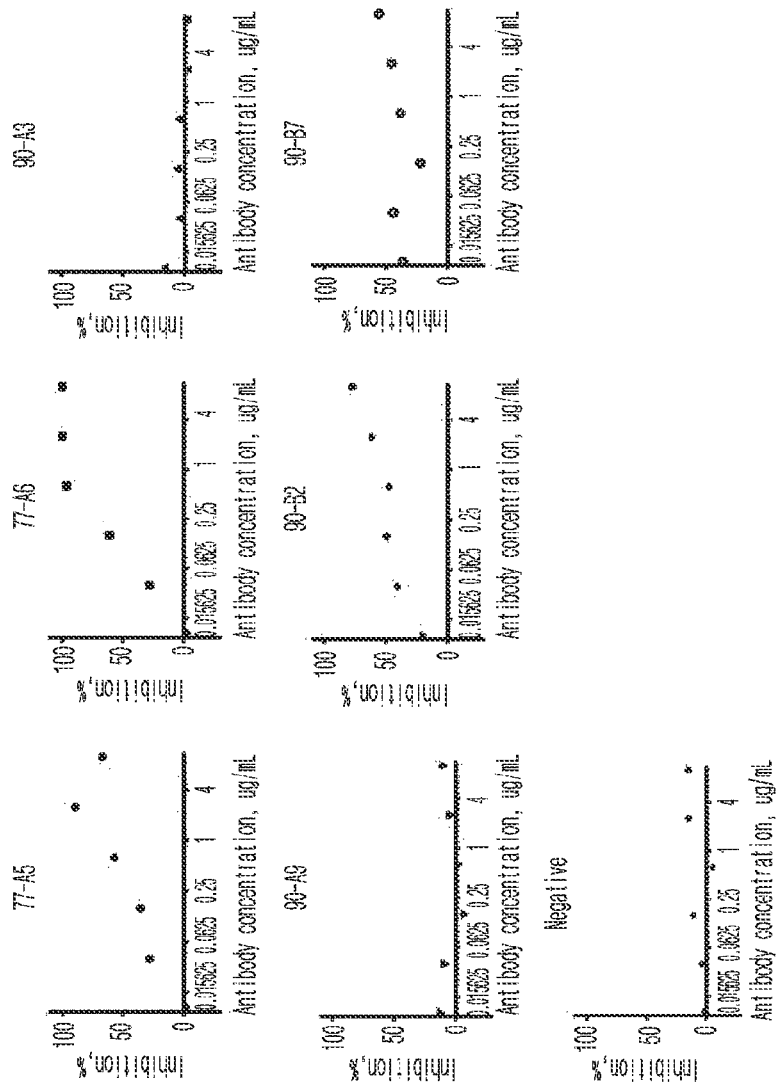
FIG. 6a is a set of graphs illustrating the neutralizing ability of 77-A5, 77-A6, 90-A3, 90-A9, 90-B2 and 90-B7 antibodies against MERS-CoV.

As a result, as shown in FIG. 6a, FIG. 6b and Table 3, 77-A5, 77-A6, 90-B2, 90-B7, 90-F1, 90-F2, and 90-E5 antibodies demonstrated neutralizing capacity against MERS-CoV. Among them, 90-F1 antibody showed the highest neutralizing capacity (FIG. 6a, FIG. 6b and Table 3). The results were the same for all MERS-CoV strains (EMC, KNIH-002, KNIH-016, and KNIH-042 strains).

Experimental Example 4: Physicochemical Characterization of Antibodies

The physicochemical characteristics of the antibodies 77-A5, 77-A6, 90-B2, 90-B7, 90-F1, and 90-F2, demon strating excellent neutralizing capacity in Experimental Examples 2 and 3, were analyzed by SEC-HPLC (size exclusion chromatography-HPLC), SPR assay (surface plasmon resonance assay) and PTS assay (protein thermal shift assay).

<4-1> Analysis of Antibody Morphology by SEC-HPLC

The antibody morphology was analyzed by using water SEC-HPLC system. Agilent Bio SEC3 was used as the HPLC column and ultraviolet absorption spectrophotometer (280 nm) was used as the detector. At this time, 10 µl of each antibody was loaded as the sample at the concentration of 1 mg/ml. The flow rate was 0.3 ml/min. 1× PBS was used as a moving phase for isocratic elution.

Figure 7:
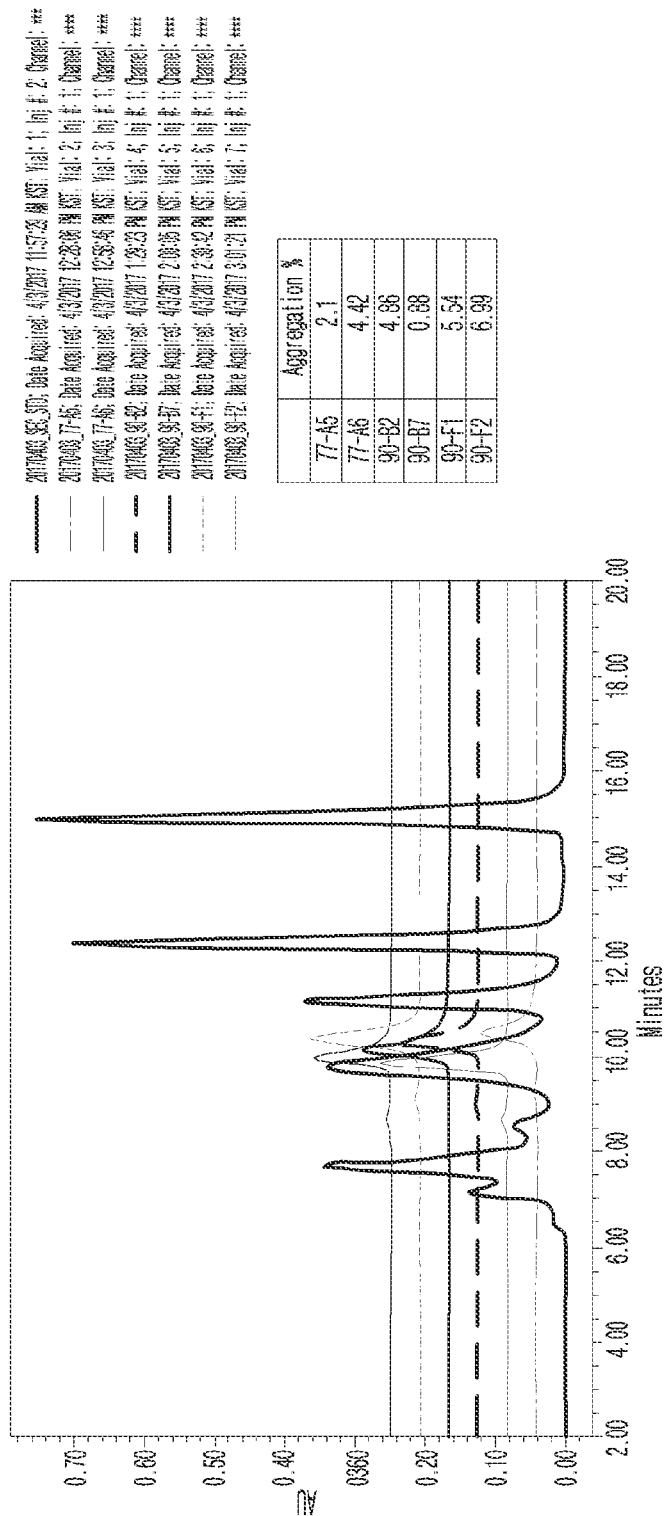
FIG. 7 is a graph illustrating the morphology of the antibodies analyzed by SEC-HPLC.

As a result, as shown in FIG. 7, 6 kinds of antibodies were in the form of a certain monomer, and coagulation was not observed (FIG. 7).

<4-2> Analysis of Antibody Avidity by SPR Assay

The avidity of the antibodies was analyzed by SPR assay using S1 antigen or RBD antigen. Particularly, S1 antigen or RBD antigen was attached on the surface of CM5 chip, to which the antibody was loaded. The association time was 3 minutes and the dissociation time was as listed in Table 4. HBS-EP was used as a running buffer, and regeneration solution was as shown in Table 4 for SPR assay.

TABLE 4

SPR assay conditions

| Antibody | Dissociation Time | Regeneration Solution |
|---|---|---|
| 77-A5 | 30 min. | 10 mM NaOH, 1M NaCl |
| 77-A6 | 6 min. | 10 mM NaOH |
| 90-B2 | 30 min. | 10 mM NaOH, 1M NaCl |
| 90-B7 | 10 min. | 10 mM NaOH, 250 mM NaCl |
| 90-F1 | 10 min. | 10 mM glycine(pH 2.0), 250 mM NaCl |
| 90-F2 | 6 min. | 10 mM NaOH, 500 mM NaCl |

Figure 8A:
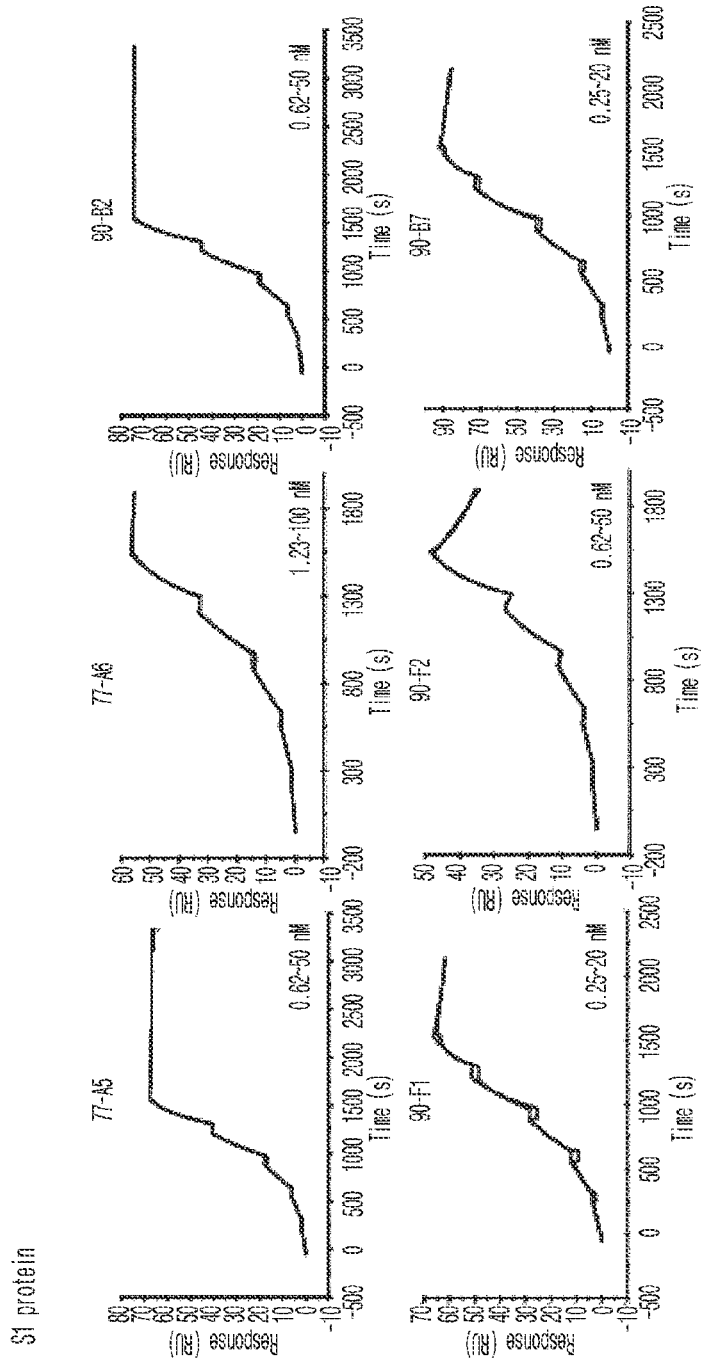
FIG. 8a is a set graphs illustrating the antigen-antibody binding affinity investigated by SPR (Surface Plasmon Resonance) assay using S1 antigen.
Figure 8B:
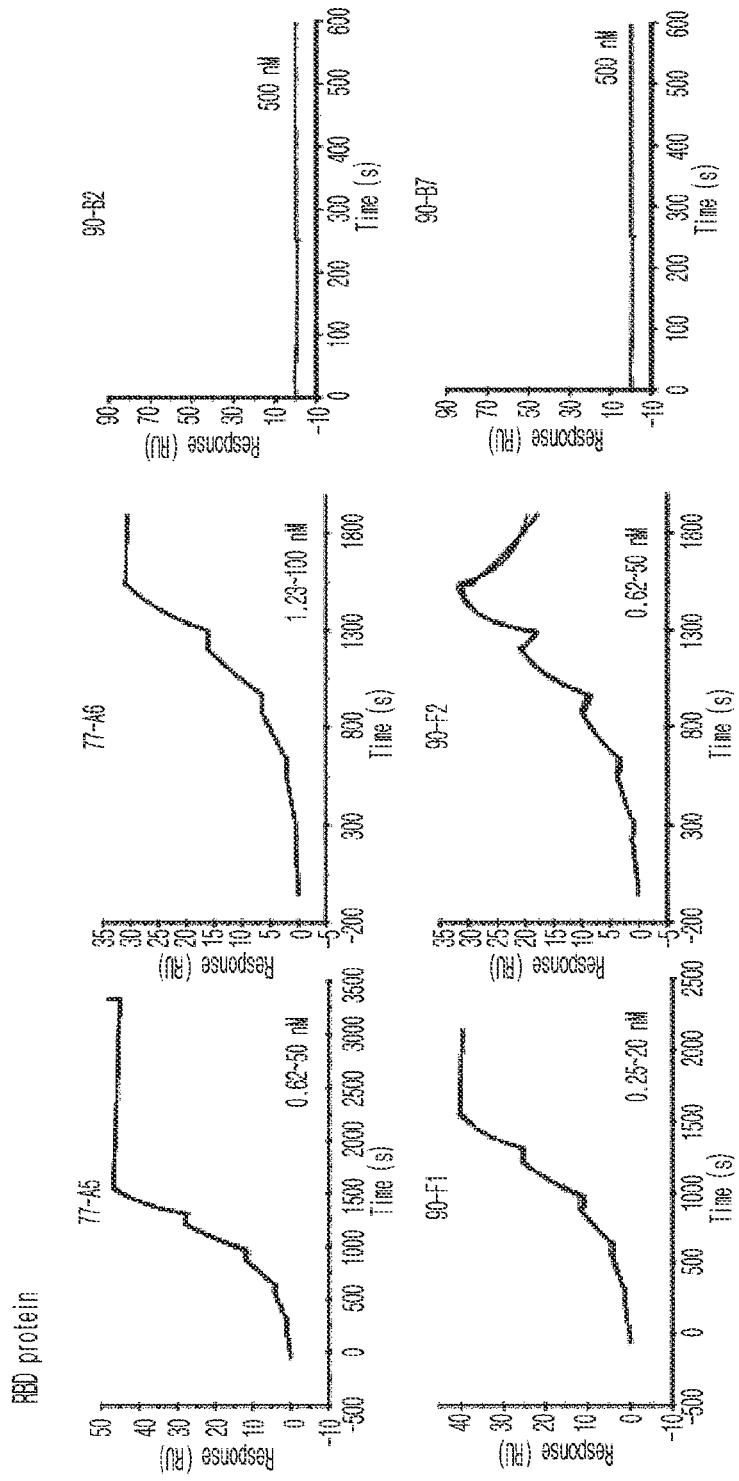
FIG. 8b is a set graphs illustrating the antigen-antibody binding affinity investigated by SPR (Surface Plasmon Resonance) assay using RBD antigen.

As a result, as shown in FIG. 8a, FIG. 8b and Table 5, the antibodies 77-A5 and 90-B2 attached with S1 antigen showed a high avidity to the S1 antigen, confirmed by the low $K_D$ value of up to 75 pM. The antibody 90-F1 attached with RBD antigen showed a high avidity to the RBD antigen, confirmed by the low $K_D$ value of up to 72 pM. In particular, 90-B2 and 90-B7 antibodies did not bind to the RBD antigen, indicating that the 90-B2 and 90-B7 antibodies were specific to the S1 antigen (FIG. 8a, FIG. 8b and Table 5).

<4-3> Investigation of Antibody Stability by PTS Assay

The antibody stability was investigated in PBS (phosphate buffered saline, pH 7.4) which included neither calcium nor magnesium. Particularly, 0.75 µg of each antibody prepared in Example 1 was used. PTS assay was performed by using Protein Thermal Shift™ Dye Kit (Catalog No. 4466038, Life technologies) according to the manufacturer's protocol.

Figure 9A:
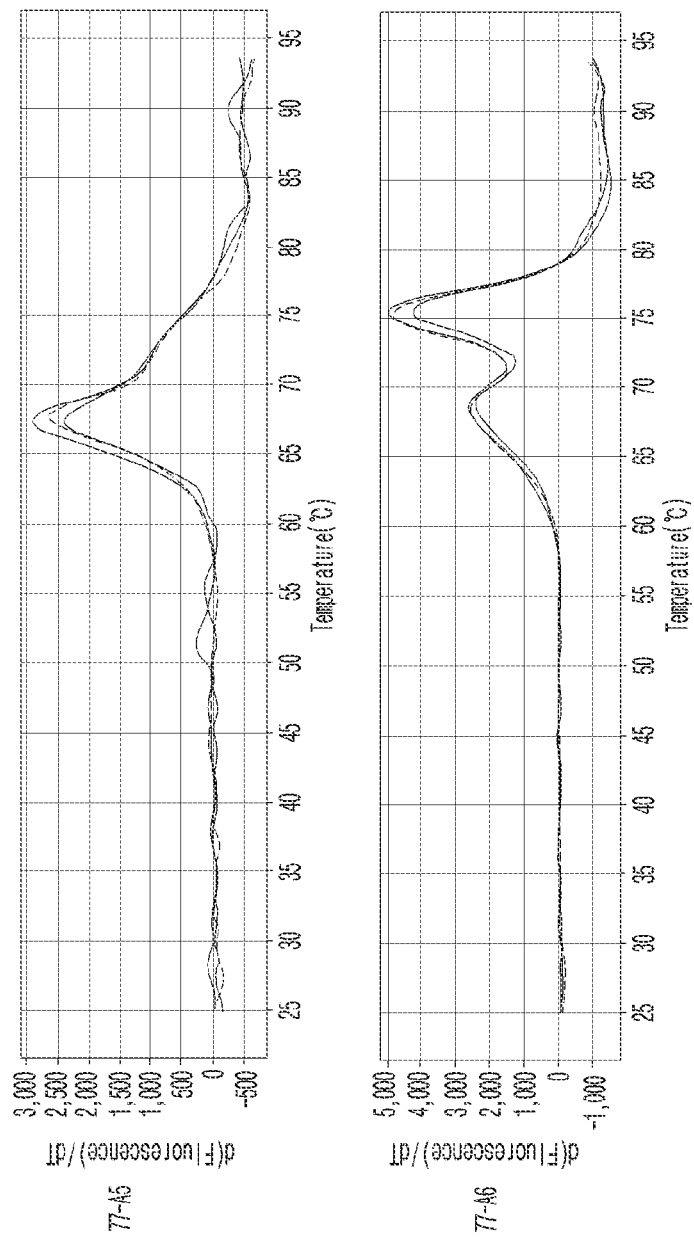
FIG. 9a is a set of graphs illustrating the thermo-stability of 77-A5 and 77-A6 antibodies investigated by PTS (Protein Thermal Shift) assay.
Figure 9B:
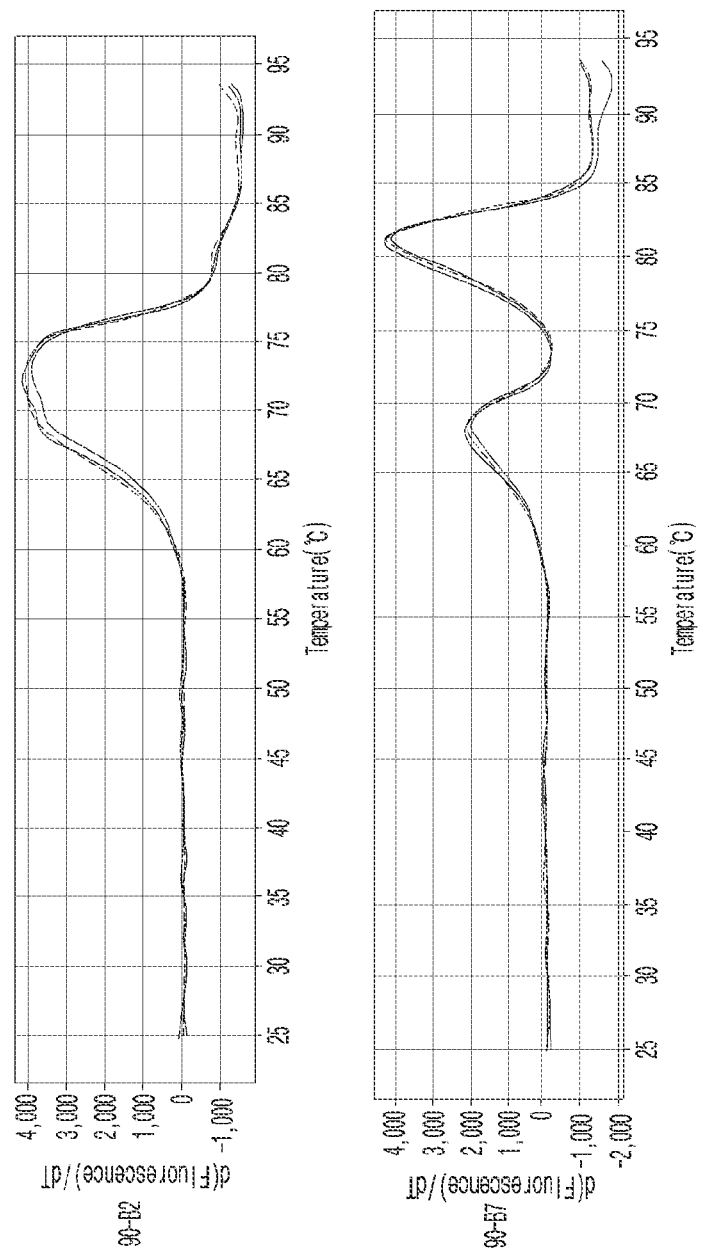
FIG. 9b is a set of graphs illustrating the thermo-stability of 90-B2 and 90-B7 antibodies investigated by PTS (Protein Thermal Shift) assay.
Figure 9C:
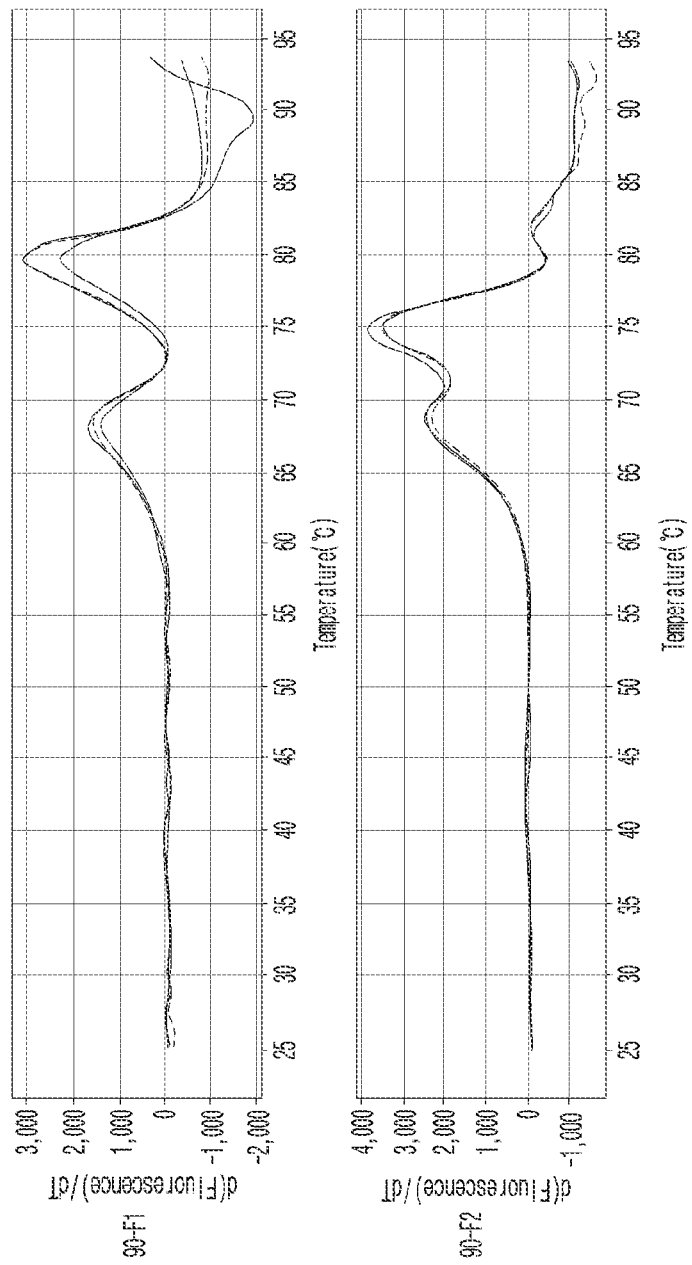
FIG. 9c is a set of graphs illustrating the thermo-stability of 90-F1, and 90-F2 antibodies investigated by PTS (Protein Thermal Shift) assay.

As a result, as shown in FIG. 9a to FIG. 9c, the melting points of 77-A5, 77-A6, 90-B2, 90-B7, 90-F1, and 90-F2 antibodies were respectively 67.52° C., 68.44° C. and 75.44° C., 72.46° C., 68.21° C. and 81.19° C., 69.21° C. and 79.81° C., and 68.89° C. and 75.10° C. Therefore, all of the six antibodies were confirmed to have a stable structure because the protein hydrophobicity was exposed at the temperature of 67.52° C. or higher (FIG. 9a to FIG. 9c).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

TABLE 5

Analysis of antibody avidity by SPR assay

| Characteristic | 77-A5 | 77-A6 | 90-B2 | 90-B7 | 90-F1 | 90-F2 |
|---|---|---|---|---|---|---|
| Avidity to S1 antigen | | | | | | |
| $K_a$(1/Ms) | $1.33 \times 10^5$ | $6.38 \times 10^4$ | $1.31 \times 10^5$ | $6.81 \times 10^5$ | $6.48 \times 10^5$ | $1.34 \times 10^5$ |
| $K_d$(1/s) | $\leq 1.00 \times 10^{-5}$ | $4.43 \times 10^{-5}$ | $\leq 1.00 \times 10^{-5}$ | $1.04 \times 10^{-4}$ | $9.88 \times 10^{-5}$ | $8.82 \times 10^{-4}$ |
| $K_D$(M) | $\leq 7.51 \times 10^{-11}$ | $6.95 \times 10^{-10}$ | $\leq 7.51 \times 10^{-11}$ | $1.53 \times 10^{-10}$ | $1.53 \times 10^{-10}$ | $6.60 \times 10^{-9}$ |
| Avidity to RBD antigen | | | | | | |
| $K_a$(1/Ms) | $1.30 \times 10^5$ | $4.67 \times 10^4$ | — | — | $3.76 \times 10^5$ | $2.38 \times 10^5$ |
| $K_d$(1/s) | $2.08 \times 10^{-5}$ | $3.15 \times 10^{-5}$ | — | — | $2.71 \times 10^{-5}$ | $1.40 \times 10^{-5}$ |
| $K_D$(M) | $1.61 \times 10^{-10}$ | $6.73 \times 10^{-10}$ | — | — | $7.20 \times 10^{-11}$ | $5.86 \times 10^{-9}$ |

What is claimed is:

1. A method for treating Middle East Respiratory Syndrome (MERS) in a subject, said method comprising:
administering to the subject an effective amount of a monoclonal antibody, the monoclonal antibody having binding specificity to Middle East Respiratory Syndrome coronavirus (MERS-CoV) spike protein, the monoclonal antibody comprising:
human immunoglobulin heavy chain constant region and human immunoglobulin light chain constant region, and
a combination of heavy chain variable region (VH) and light chain variable region (VL) selected from the group consisting of:
VH according to SEQ ID NOs: 1 and VL according to SEQ ID NOs 2;
VH according to SEQ ID NOs: 3 and VL according to SEQ ID NOs 4;
VH according to SEQ ID NOs: 9 and VL according to SEQ ID NOs 10;
VH according to SEQ ID NOs: 11 and VL according to SEQ ID NOs 12;
VH according to SEQ ID NOs: 19 and VL according to SEQ ID NOs 20; and
VH according to SEQ ID NOs: 21 and VL according to SEQ ID NOs 22.

2. The method of claim 1, wherein the MERS-COV spike protein comprises an amino acid sequence represented by SEQ.ID. NO: 23.

3. The method of claim 2, wherein the combination of the VH and the VL have binding specificity to a region of the MERS-COV spike protein comprising the 1st to 757th amino acids from the N-terminus of the MERS-COV spike protein.

4. A method for detecting Middle East Respiratory Syndrome coronavirus (MERS-COV) antigen, said method comprising:
performing an antigen-antibody reaction using a monoclonal antibody, the monoclonal antibody having binding specificity to Middle East Respiratory Syndrome coronavirus (MERS-CoV) spike protein, the monoclonal antibody comprising:
human immunoglobulin heavy chain constant region and human immunoglobulin light chain constant region, and
a combination of heavy chain variable region (VH) and light chain variable region (VL) selected from the group consisting of:
VH according to SEQ ID NOs: 1 and VL according to SEQ ID NOs 2;
VH according to SEQ ID NOs: 3 and VL according to SEQ ID NOs 4;
VH according to SEQ ID NOs: 9 and VL according to SEQ ID NOs 10;
VH according to SEQ ID NOs: 11 and VL according to SEQ ID NOs 12;
VH according to SEQ ID NOs: 19 and VL according to SEQ ID NOs 20; and
VH according to SEQ ID NOs: 21 and VL according to SEQ ID NOs 22.

5. The method of claim 4, wherein the MERS-COV spike protein comprises an amino acid sequence represented by SEQ.ID. NO: 23.

6. The method of claim 5, wherein the combination of the VH and the VL have binding specificity to a region of the MERS-COV spike protein comprising the 1st to 757th amino acids from the N-terminus of the MERS-COV spike protein.

7. A method, comprising:
contacting Middle East Respiratory Syndrome coronavirus (MERS-COV) with a monoclonal antibody, the monoclonal antibody having binding specificity to MERS-COV spike protein, the monoclonal antibody comprising:
human immunoglobulin heavy chain constant region and human immunoglobulin light chain constant region, and
a combination of heavy chain variable region (VH) and light chain variable region (VL) selected from the group consisting of:
VH having an amino acid sequence according to SEQ ID NOs: 1 and VL having an amino acid sequence according to SEQ ID NOs 2;
VH having an amino acid sequence according to SEQ ID NOs: 3 and VL having an amino acid sequence according to SEQ ID NOs 4;
VH having an amino acid sequence according to SEQ ID NOs: 9 and VL having an amino acid sequence according to SEQ ID NOs 10;
VH having an amino acid sequence according to SEQ ID NOs: 11 and VL having an amino acid sequence according to SEQ ID NOs 12;
VH having an amino acid sequence according to SEQ ID NOs: 19 and VL having an amino acid sequence according to SEQ ID NOs 20; and
VH having an amino acid sequence according to SEQ ID NOs: 21 and VL having an amino acid sequence according to SEQ ID NOs 22.

8. A monoclonal antibody having binding specificity to Middle East Respiratory Syndrome coronavirus (MERS-COV) spike protein, the monoclonal antibody, comprising:

heterologous human immunoglobulin G (IgG) heavy chain constant region, and a combination of heavy chain variable region (VH) and light chain variable region (VL) selected from the group consisting of:

VH according to SEQ ID NOs: 1 and VL according to SEQ ID NOs 2;

VH according to SEQ ID NOs: 3 and VL according to SEQ ID NOs 4;

VH according to SEQ ID NOs: 9 and VL according to SEQ ID NOs 10;

VH according to SEQ ID NOs: 11 and VL according to SEQ ID NOs 12;

VH according to SEQ ID NOs: 19 and VL according to SEQ ID NOs 20; and

VH according to SEQ ID NOs: 21 and VL according to SEQ ID NOs 22.

9. A composition for binding Middle East Respiratory Syndrome coronavirus (MERS-COV) spike protein, the composition comprising:

an excipient; and an effective amount of the monoclonal antibody of claim 8 disposed in the excipient, the monoclonal antibody having binding specificity to Middle East Respiratory Syndrome coronavirus (MERS-COV) spike protein, the monoclonal antibody comprising:

heterologous human immunoglobulin G (IgG) heavy chain constant region, and a combination of heavy chain variable region (VH) and light chain variable region (VL) selected from the group consisting of:

VH according to SEQ ID NOs: 1 and VL according to SEQ ID NOs 2;

VH according to SEQ ID NOs: 3 and VL according to SEQ ID NOs 4;

VH according to SEQ ID NOs: 9 and VL according to SEQ ID NOs 10;

VH according to SEQ ID NOs: 11 and VL according to SEQ ID NOs 12;

VH according to SEQ ID NOs: 19 and VL according to SEQ ID NOs 20; and

VH according to SEQ ID NOs: 21 and VL according to SEQ ID NOs 22.

* * * * *